United States Patent
Le et al.

(10) Patent No.: US 10,591,478 B2
(45) Date of Patent: Mar. 17, 2020

(54) METHODS FOR MOLECULAR CLASSIFICATION OF FATTY LIVER BY HIGH-THROUGHPUT PROTEIN POST-TRANSLATIONAL MODIFICATIONS

(71) Applicant: ROSEMAN UNIVERSITY OF HEALTH SCIENCES, Las Vegas, NV (US)

(72) Inventors: Thuc T. Le, Las Vegas, NV (US); Yasuyo Urasaki, Las Vegas, NV (US); Ronald R. Fiscus, Las Vegas, NV (US)

(73) Assignee: Roseman University of Health Sciences, Las Vegas, NV (US)

( * ) Notice: Subject to any disclaimer, the term of this patent is extended or adjusted under 35 U.S.C. 154(b) by 0 days.

(21) Appl. No.: 15/755,399

(22) PCT Filed: Aug. 25, 2016

(86) PCT No.: PCT/US2016/048615
§ 371 (c)(1),
(2) Date: Feb. 26, 2018

(87) PCT Pub. No.: WO2017/035323
PCT Pub. Date: Mar. 2, 2017

(65) Prior Publication Data
US 2018/0259515 A1   Sep. 13, 2018

Related U.S. Application Data

(60) Provisional application No. 62/209,344, filed on Aug. 25, 2015.

(51) Int. Cl.
*G01N 33/561*   (2006.01)
*G01N 33/573*   (2006.01)

(52) U.S. Cl.
CPC .... *G01N 33/561* (2013.01); *C12Y 103/99003* (2013.01); *C12Y 203/01043* (2013.01); *C12Y 203/0301* (2013.01); *C12Y 207/01011* (2013.01); *C12Y 207/11001* (2013.01); *C12Y 207/11024* (2013.01); *C12Y 207/11025* (2013.01); *C12Y 207/11026* (2013.01); *C12Y 402/01017* (2013.01); *G01N 33/573* (2013.01); *G01N 2333/47* (2013.01); *G01N 2333/4703* (2013.01); *G01N 2333/90206* (2013.01); *G01N 2333/91045* (2013.01); *G01N 2333/91057* (2013.01); *G01N 2333/91205* (2013.01); *G01N 2333/91215* (2013.01); *G01N 2333/988* (2013.01); *G01N 2440/00* (2013.01); *G01N 2440/10* (2013.01); *G01N 2440/14* (2013.01); *G01N 2440/38* (2013.01); *G01N 2800/085* (2013.01); *G01N 2800/52* (2013.01)

(58) Field of Classification Search
CPC .... C12Y 103/99003; C12Y 203/01043; C12Y 203/0301; C12Y 207/01011; C12Y 207/11001; C12Y 207/11024; C12Y 207/11025; C12Y 207/11026; C12Y 402/01017; G01N 2333/47; G01N 2333/4703; G01N 2333/90206; G01N 2333/91045; G01N 2333/91057; G01N 2333/91205; G01N 2333/91215; G01N 2333/988; G01N 2440/00; G01N 2440/10; G01N 2440/14; G01N 2440/38; G01N 2800/085; G01N 2800/52; G01N 33/561; G01N 33/573
See application file for complete search history.

(56) References Cited

FOREIGN PATENT DOCUMENTS

WO    2007136822 A2    11/2007

OTHER PUBLICATIONS

Chen et al. Capillary isoelectric-focusing immunoassays to study dynamic oncoprotein phosphorylation and drug response to targeted therapies in non-small cell lung cancer. Mol Cancer Ther., Nov. 2013. vol. 12, No. 11, pp. 1-23. (Year: 2013).*
Tikhanovich et al. Regulation of FOXO3 by phosphorylation and methylation in Hepatitis C virus infection and alcohol exposure. Hepatology, Jan. 2014. vol. 59, No. 1, pp. 1-23. (Year: 2014).*
Westerbacka et al. Genes Involved in Fatty Acid Partitioning and Binding, Lipolysis, Monocyte/Macrophage Recruitment, and Inflammation Are Overexpressed in the Human Fatty Liver of Insulin-Resistant Subjects. Diabetes, Nov. 2007, vol. 56, pp. 2759-2765. (Year: 2007).*
Koo. Nonalcoholic fatty liver disease: molecular mechanisms for the hepatic steatosis. CMH, 2013. vol. 19, pp. 210-215. (Year: 2013).*
Tolman et al. Treatment of non-alcoholic fatty liver disease. Therapeutics and Clinical Risk Management, 2007. vol. 3, No. 6, pp. 1153-1163. (Year: 2007).*
International Search Report and Written Opinion received in PCT Application No. PCT/US2016/048615, dated Dec. 23, 2016: 18 pages.
Johlfs et al., Capillary Isoelectric Focusing Immunoassay for Fat Cell Differentiation Proteomics. PLoS One. Jul. 1, 2015;10(7):e0132105.
Svoboda et al., Changes in hepatic protein expression in spontaneously hypertensive rats suggest early stages of non-alcoholic fatty liver disease. J Proteomics. Mar. 16, 2012;75(6):1752-63.
Urasaki et al., Molecular classification of fatty liver by high-throughput profiling of protein post-translational modifications. J Pathol. Apr. 2016;238(5):641-50.
Byrne and Hoehn, Subclassification of fatty liver by its pathogenesis: cIEFing is beiieving#, J Pathol. 2016; 239(1): 3-5.

* cited by examiner

*Primary Examiner* — Marcela M Cordero Garcia
(74) *Attorney, Agent, or Firm* — Hogan Lovells US LLP

(57) ABSTRACT

The present invention is directed towards methods for treating non-alcoholic fatty liver disease (NAFLD) in a patient and determining prognosis of NAFLD in a patient.

42 Claims, 14 Drawing Sheets

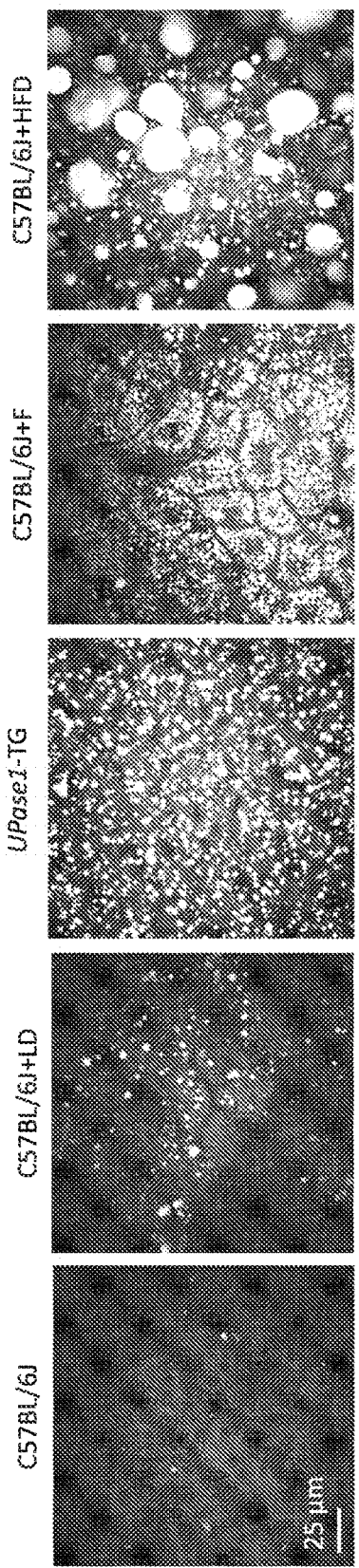
FIG. 1 Assessment of hepatic steatosis with CARS microscopy

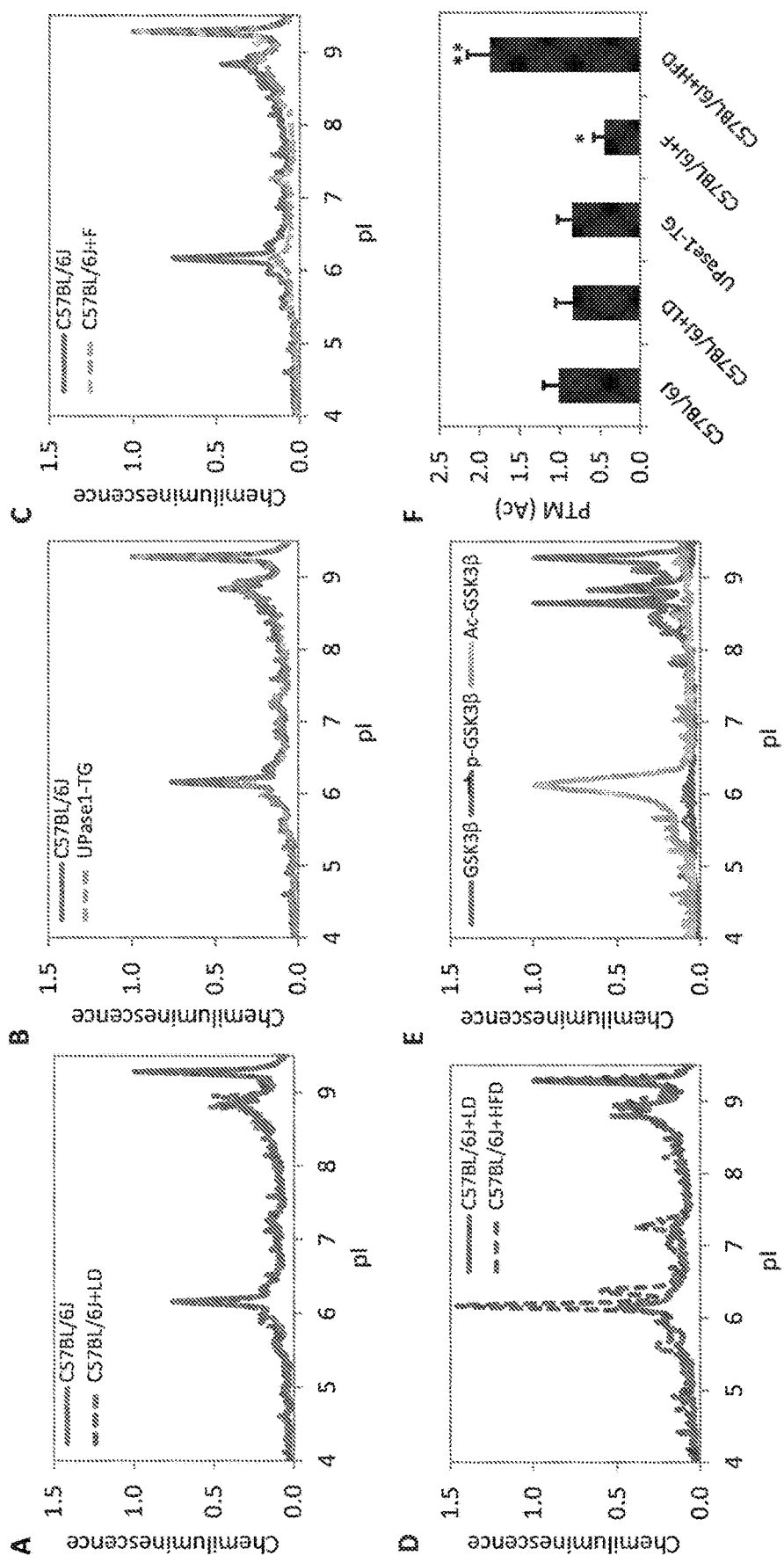
FIG. 2 PTM profile of GSK3β as a function of fatty liver tissues

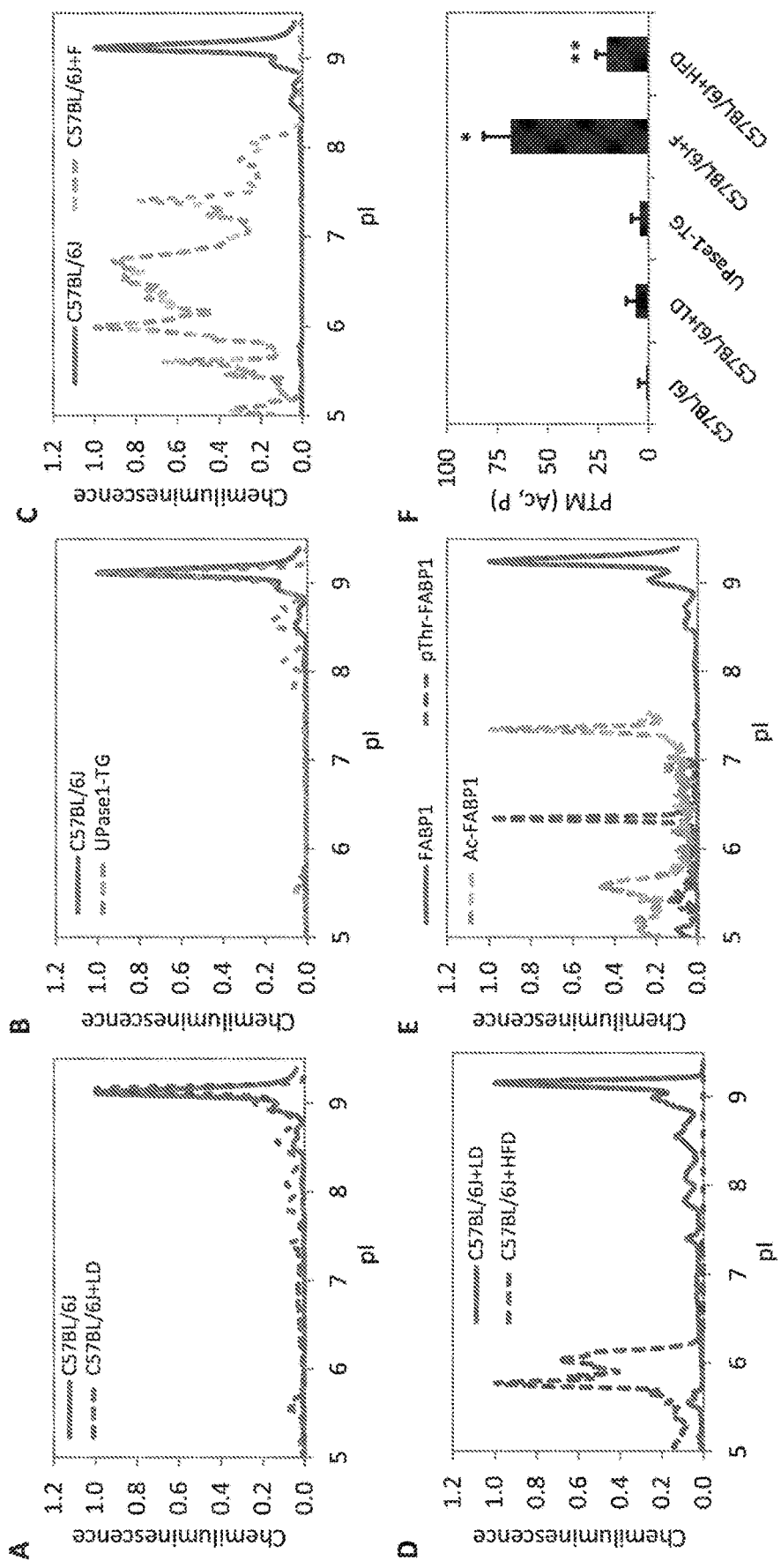
FIG. 3 PTM profile of FABP1 as a function of fatty liver tissues

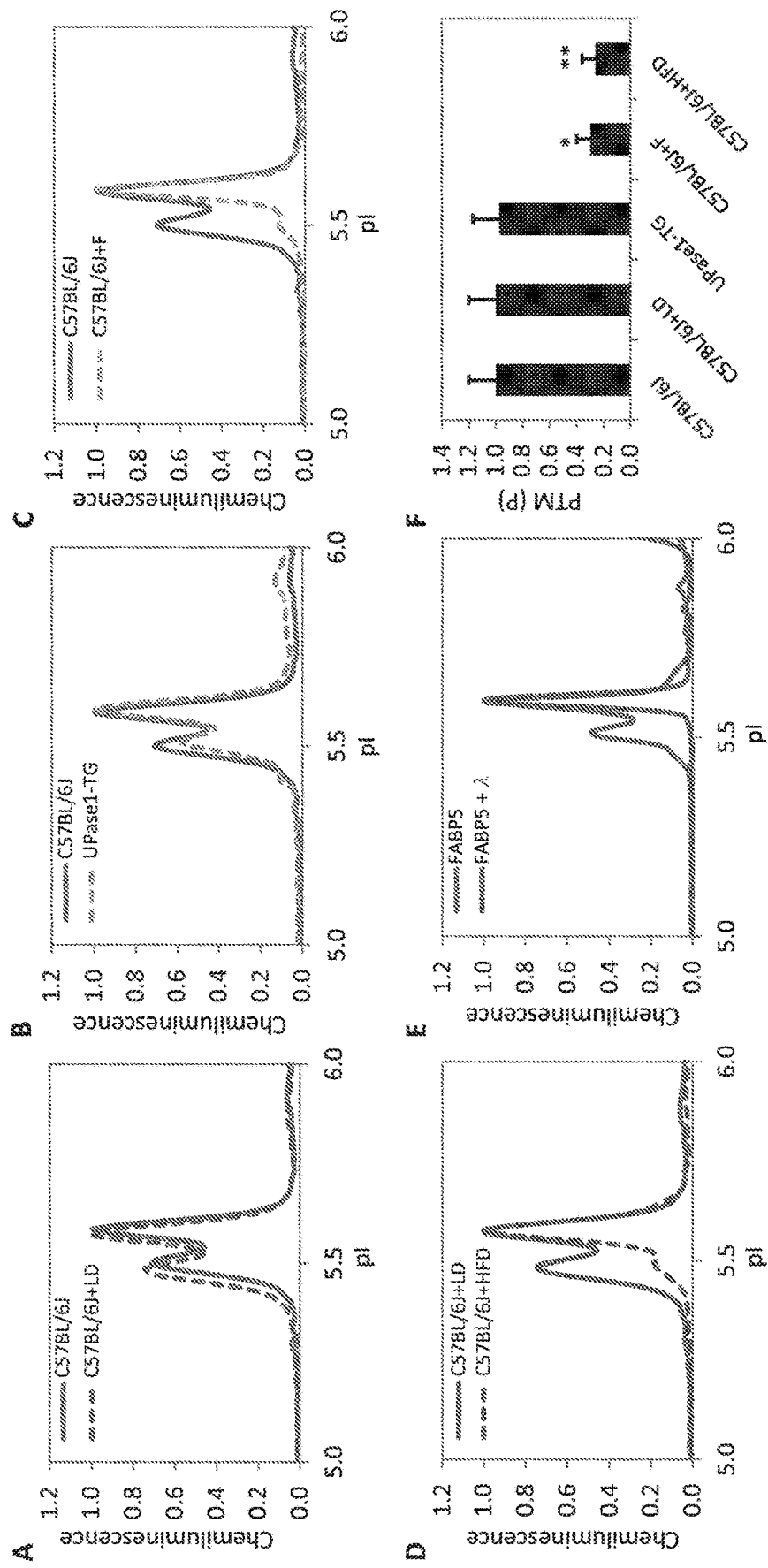
FIG. 4 PTM profile of FABP5 as a function of fatty liver tissues

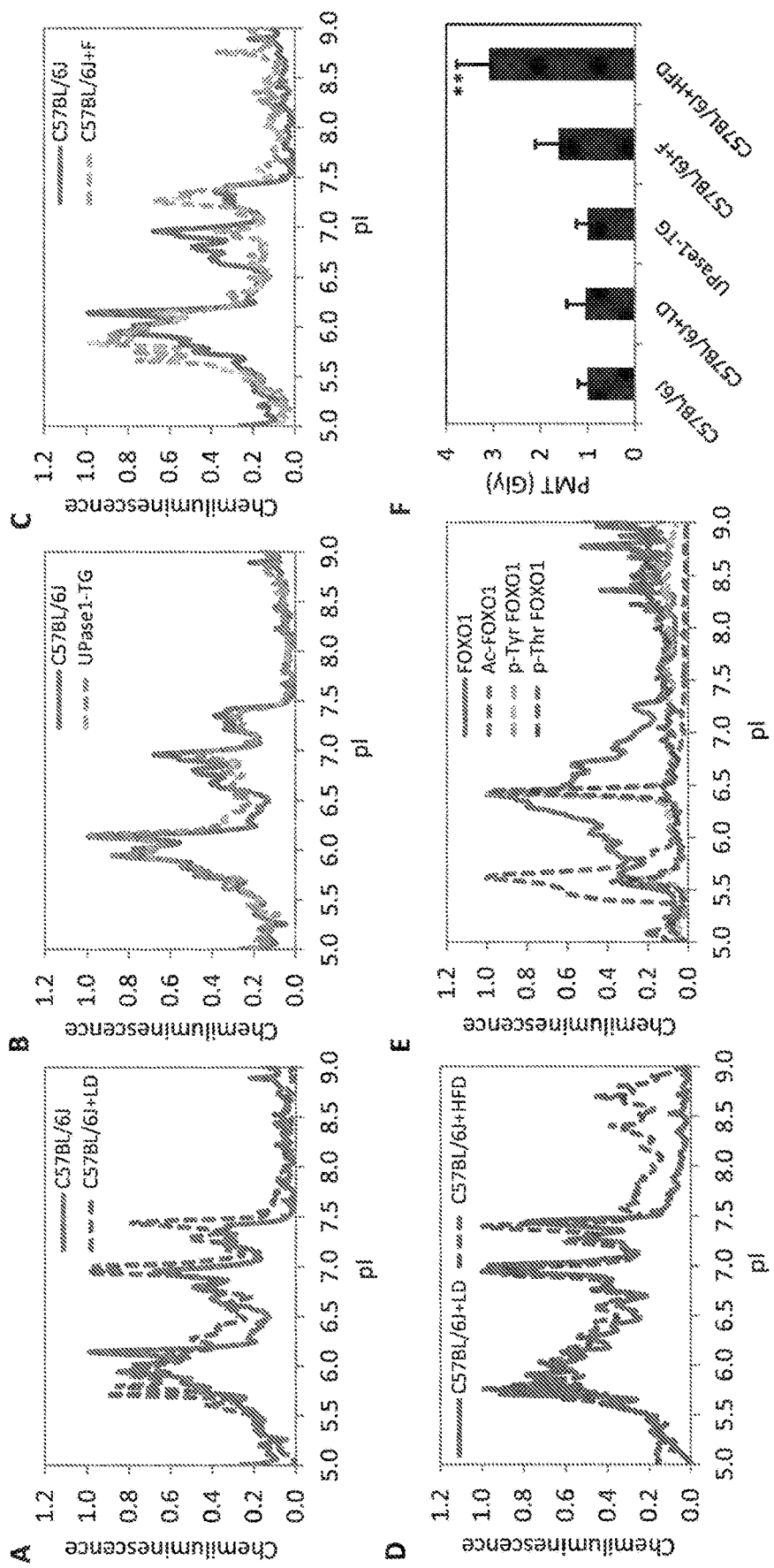
FIG. 5 PTM profile of FOXO1 as a function of fatty liver tissues

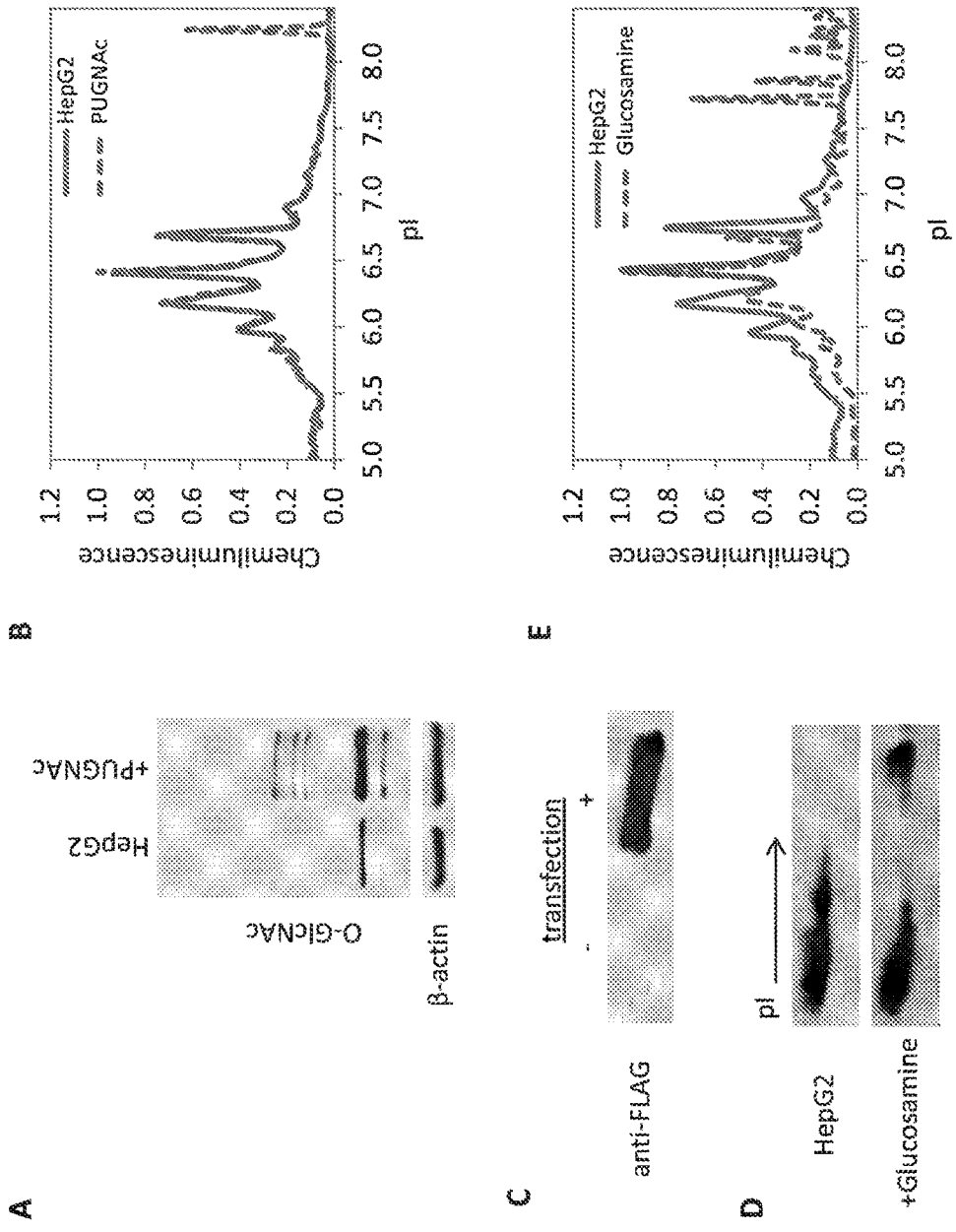
FIG. 6 Detection of FOXO1 glycosylation with 2D Western blot and cIEF immunoassays

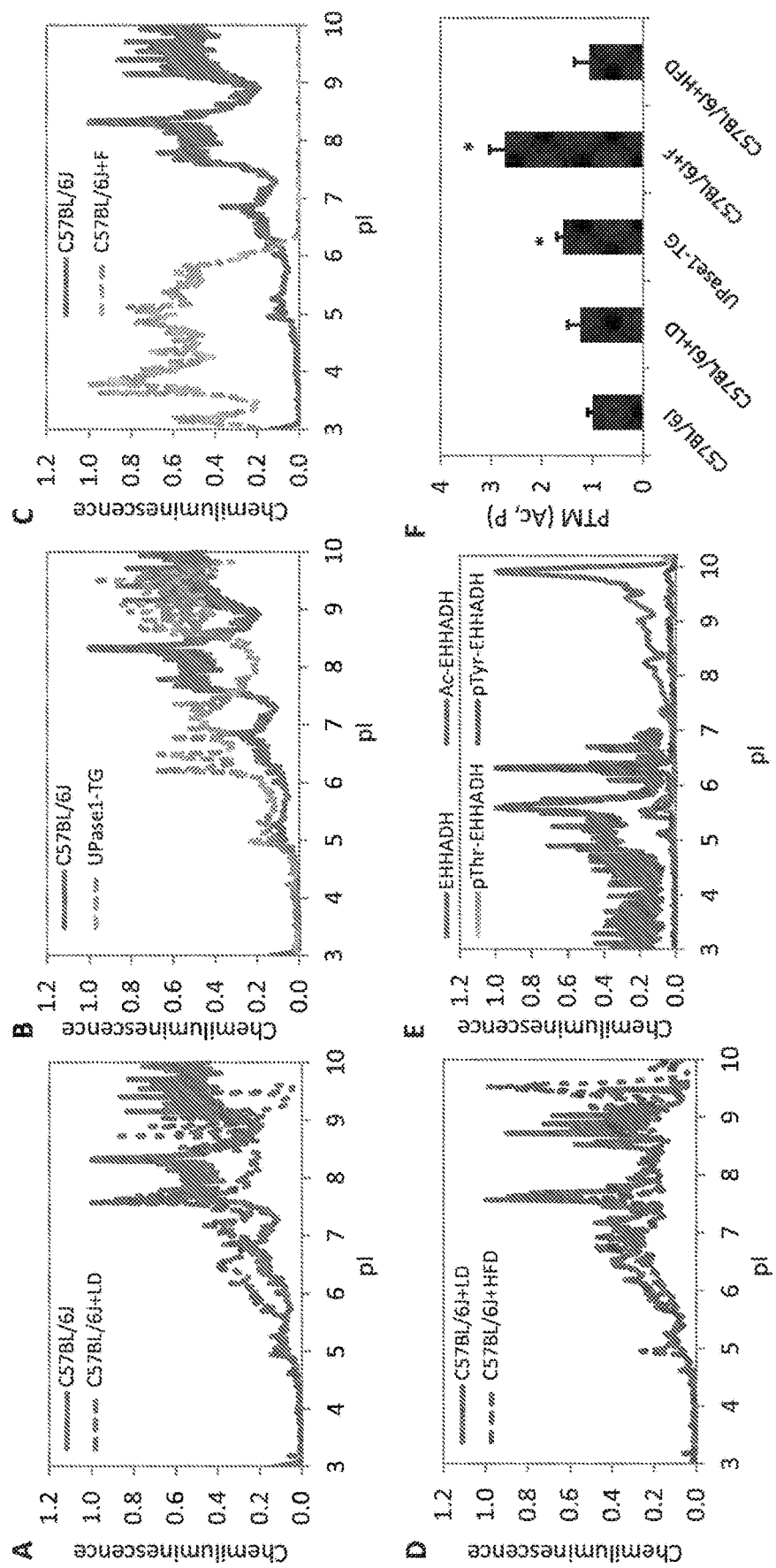
FIG. 7 PTM profile of EHHADH as a function of fatty liver tissues

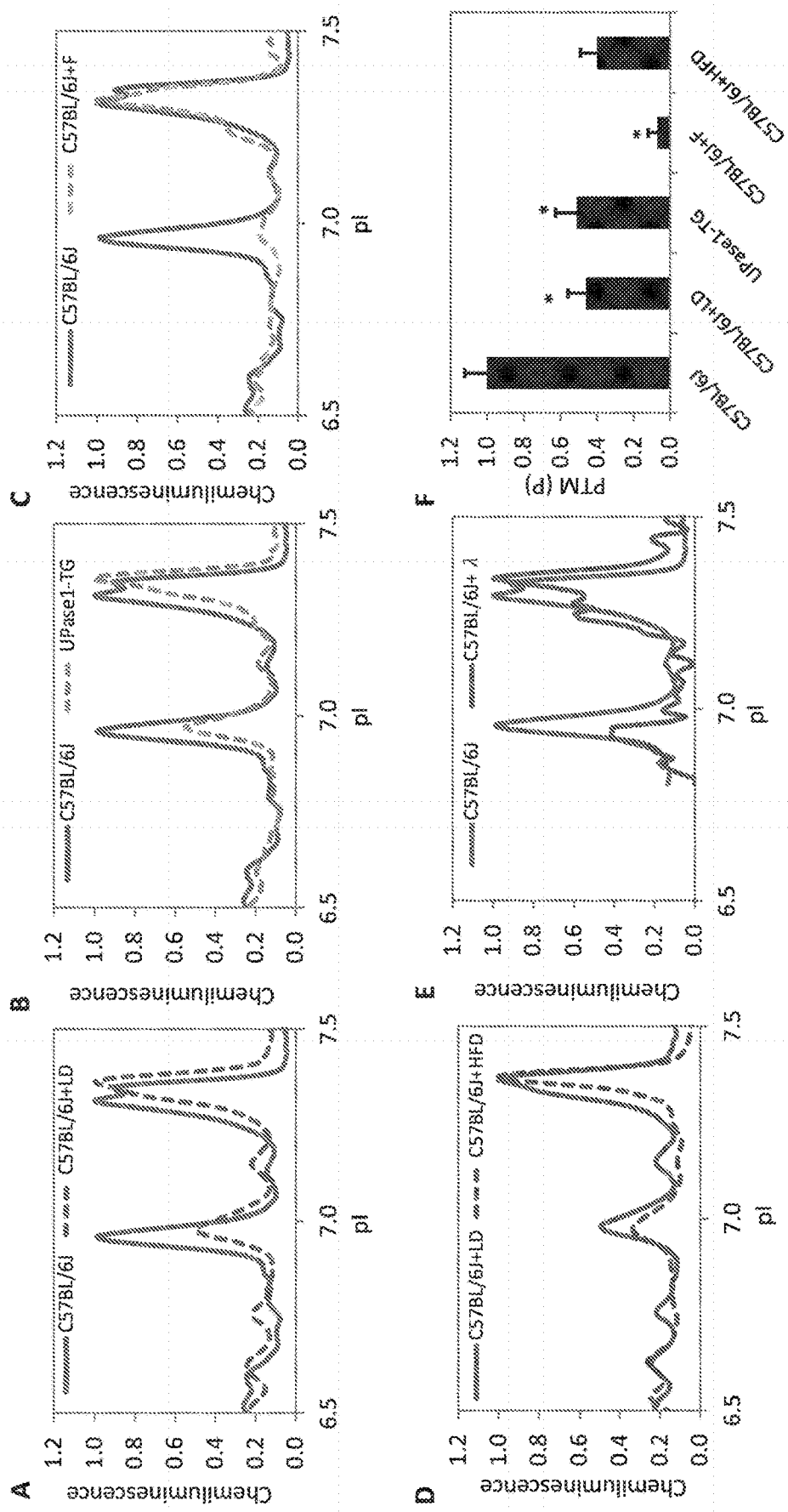
FIG. 8 PTM profile of PFK1 as a function of fatty liver tissues

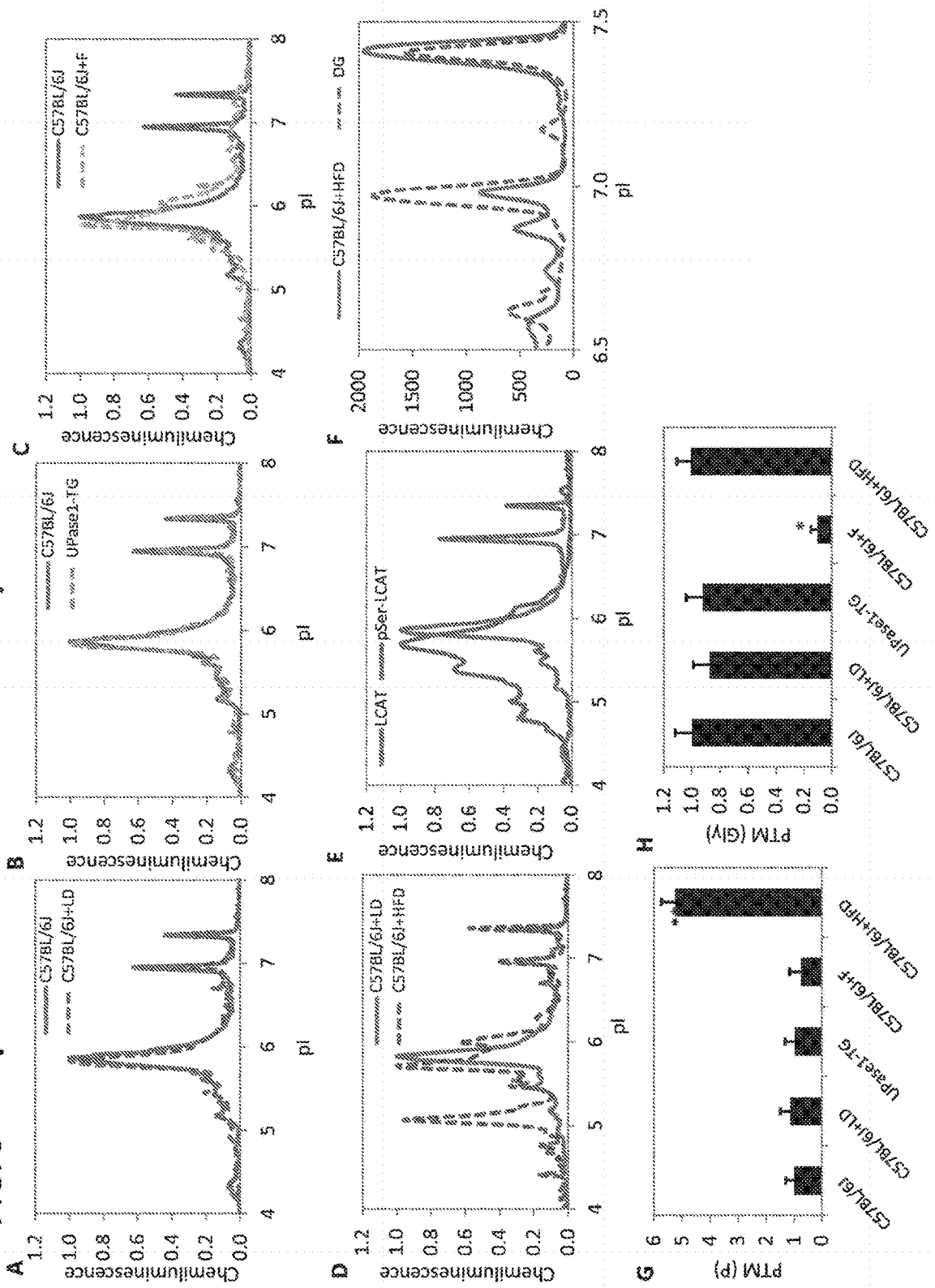
FIG. 9 PTM profile of LCAT as a function of fatty liver tissues

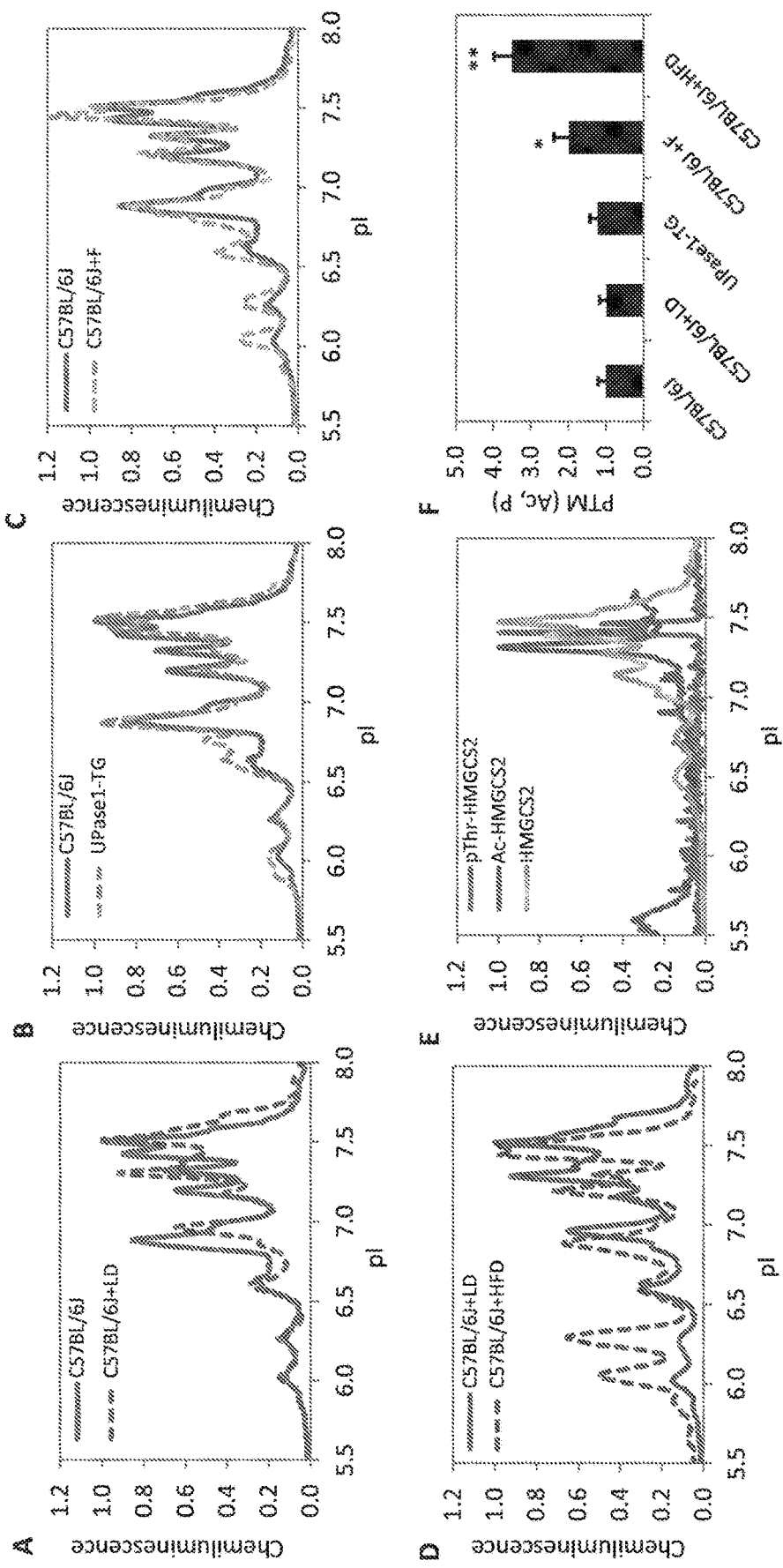
FIG. 10 PTM profile of HMGCS2 as a function of fatty liver tissues

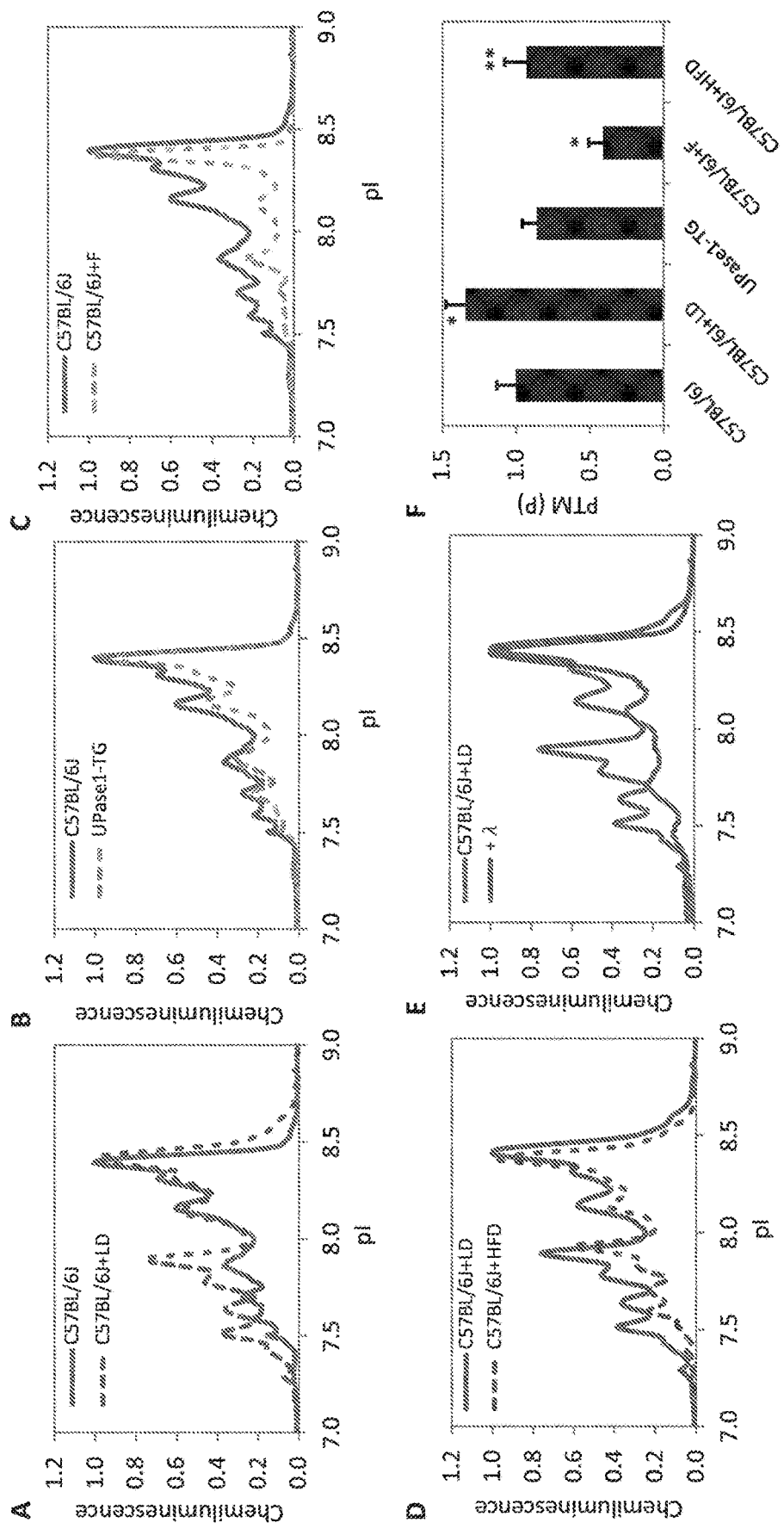
FIG. 11 PTM profile of ChREBP as a function of fatty liver tissues

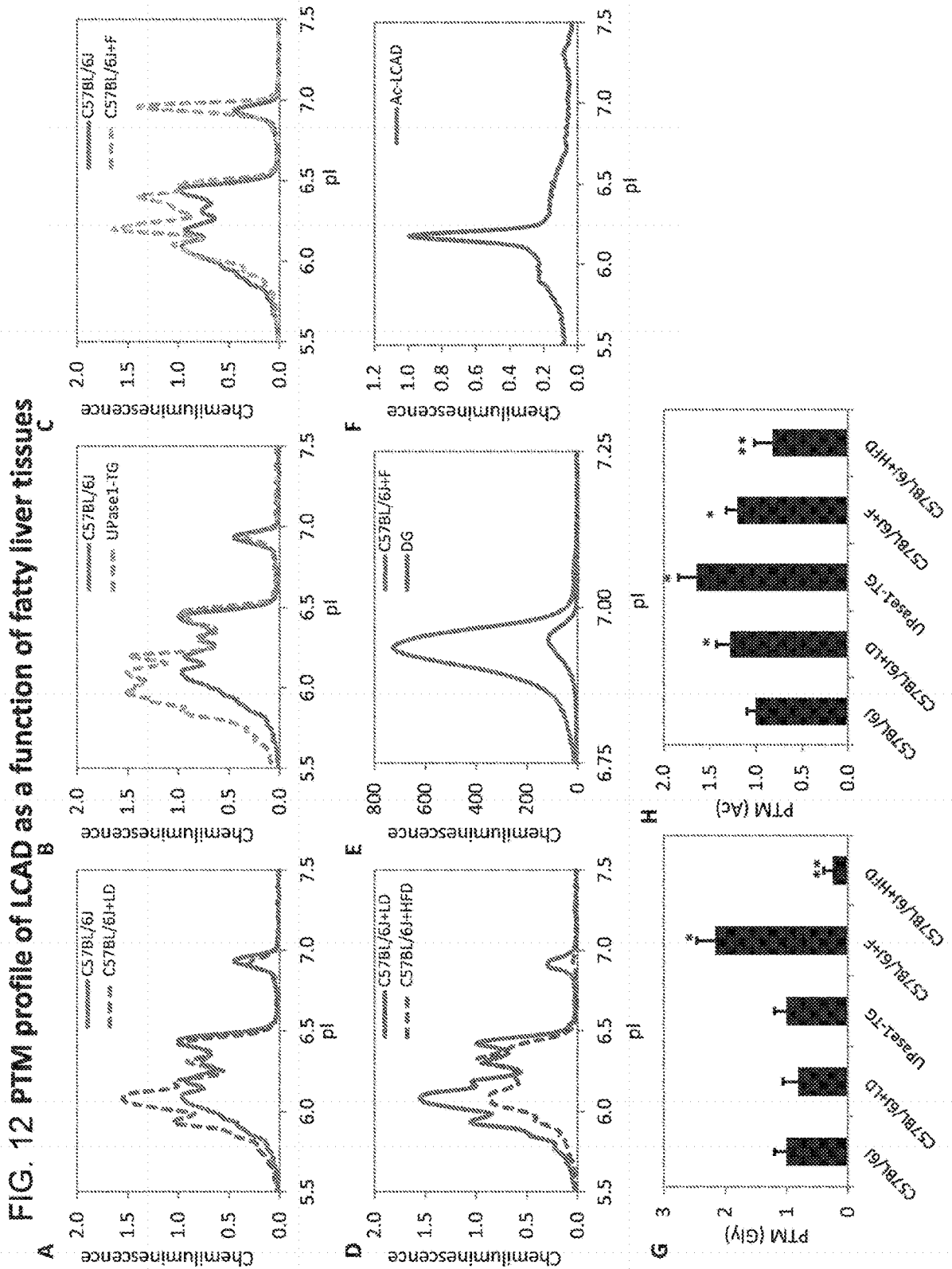
FIG. 12 PTM profile of LCAD as a function of fatty liver tissues

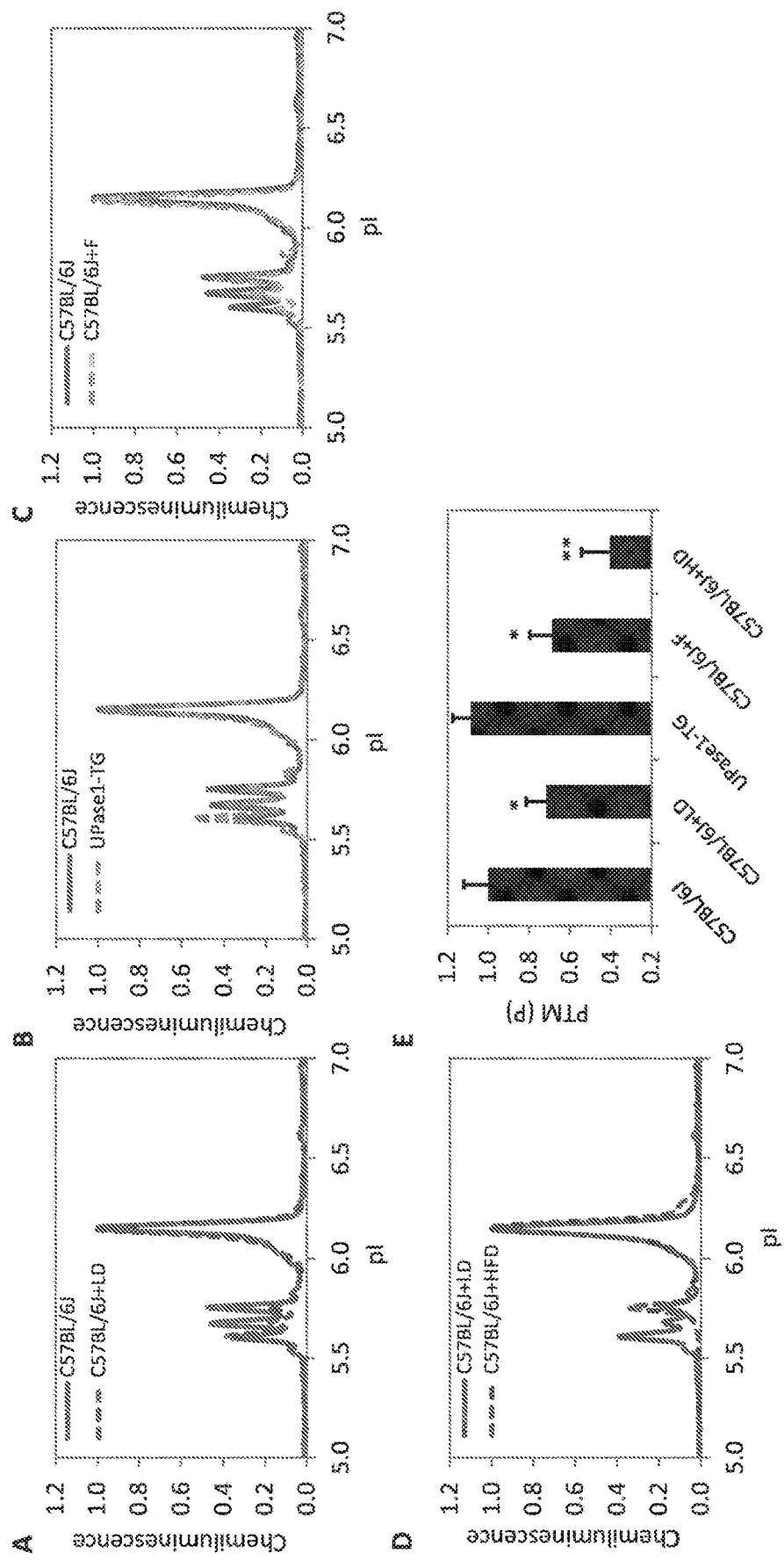
FIG. 13 PTM profile of Akt as a function of fatty liver tissues

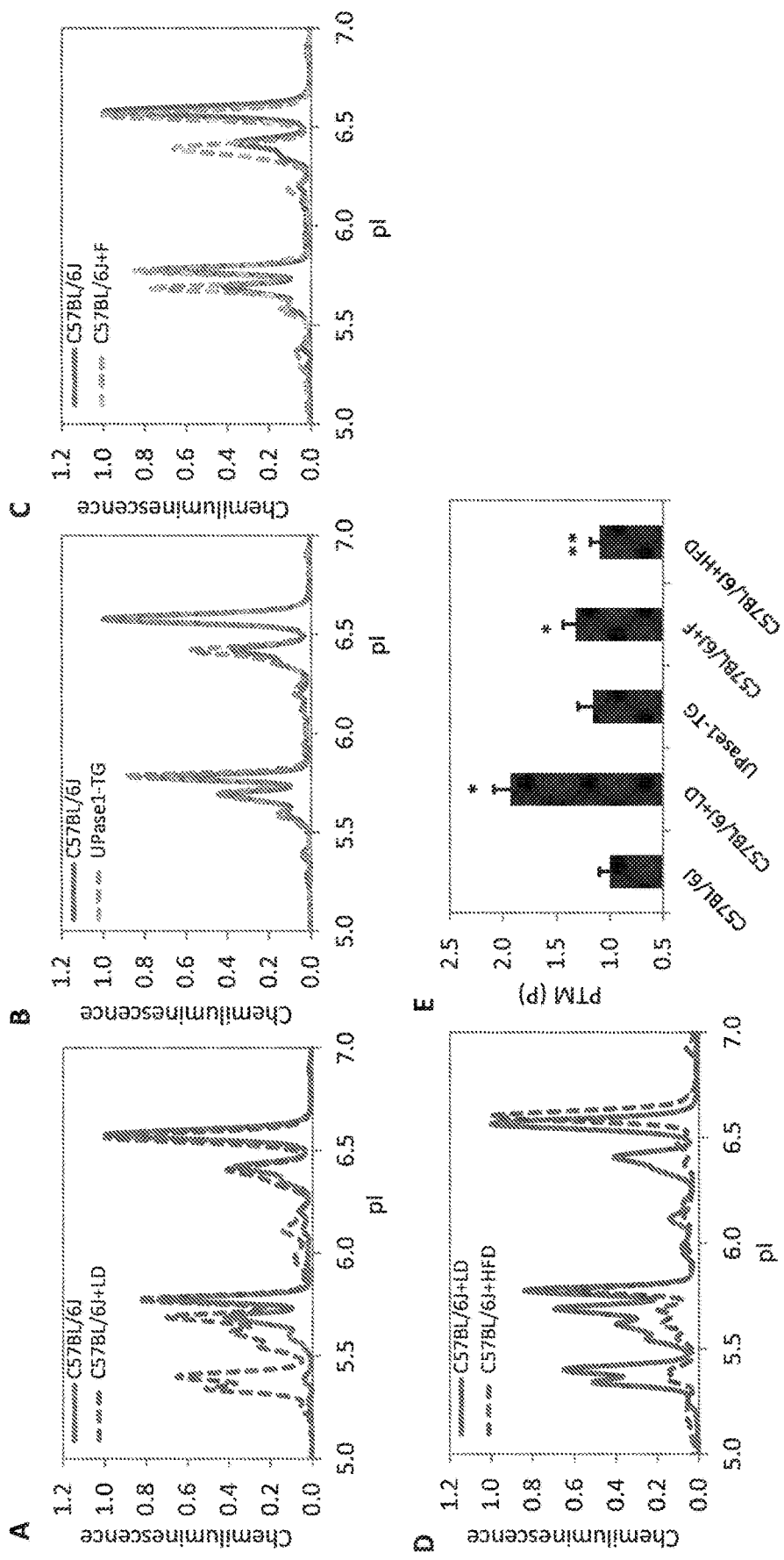
FIG. 14 PTM profile of ERK1/2 as a function of fatty liver tissues

METHODS FOR MOLECULAR CLASSIFICATION OF FATTY LIVER BY HIGH-THROUGHPUT PROTEIN POST-TRANSLATIONAL MODIFICATIONS

RELATED APPLICATIONS

This application is a National Stage application under 35 U.S.C. 371 of PCT International Application No. PCT/US2016/048615, filed Aug. 25, 2016, which claims the benefit of U.S. Provisional Application No. 62/209,344, filed Aug. 25, 2015 the entire disclosure of which is hereby incorporated by reference herein.

DESCRIPTION

Technical Field

The present invention is directed to methods for detecting post-translational modifications to classify and diagnose non-alcoholic fatty liver disease (NAFLD). In particular, the present invention is directed to methods for detecting progression, prognosis, and determining appropriate treatments for NAFLD.

Background of the Invention

Non-alcoholic fatty liver disease (NAFLD) is associated with major health risks and has complex pathogenesis. NAFLD is an established risk factor for non-alcoholic steatohepatitis, cirrhosis, hepatocellular carcinoma, and liver failure. NAFLD is also associated with increased risks for the development of dyslipidemia, type 2 diabetes mellitus, and hypertension. A hallmark of NAFLD is hepatic steatosis, or the accumulation of lipid droplets (LD) within hepatocytes. Hepatic steatosis is a consequence of multiple factors including excessive free fatty acid uptake, increased de novo lipid synthesis, reduced fatty acid oxidation, reduced fatty acid export, impaired insulin-mediated suppression of gluconeogenesis, and others. Secreted adipokines due to adipose tissue inflammation can induce liver insulin resistance leading to excessive gluconeogenesis. Drugs and toxins can impair fatty acid β-oxidation or reduce the export of fatty acid and cholesterol. Due to the complex pathogenesis, it is unlikely that the causes of NAFLD are the same in every patient.

The diagnosis and treatment of NAFLD remain clinically challenging. The presence of NAFLD generally does not cause any specific symptom in patients. Diagnosis of NAFLD often starts in patients with obesity, metabolic syndrome, or type 2 diabetes mellitus who exhibit insulin resistance or chronic elevation of serum alanine aminotransferase/aspartate aminotransferase (ALT/AST) ratio. However, ALT/AST ratio is not a reliable diagnosis because many NAFLD patients exhibit normal ALT/AST ratios. Imaging ultrasound is another possible means to detect hepatic steatosis, but this detection method is highly insensitive. The current gold standard for NAFLD diagnosis is histological pathology of liver tissues biopsies. Hepatic steatosis is confirmed when 5% or more of hepatocytes contain intracellular lipid droplet accumulation. Macrovesicular steatosis describes large LD accumulation that displaces and distorts the nucleus. In contrast, microvesicular steatosis describes small LD accumulation that does not affect the location or shape of the nucleus. Current diagnosis methods for NAFLD do not provide any insight into their pathogenesis. Preventing and reversing hepatic steatosis are logical means to treat NAFLD. Currently, clinical treatment of NAFLD has been limited to the management of associated conditions such as diabetes, hyperlipidemia, and insulin resistance. Thus, there is a need for methods capable of providing accurate diagnosis of the causes of hepatic steatosis, so that therapeutic intervention strategies can be effectively developed. The ability to document changes to cellular protein PTM profiles represents a new frontier in personalized molecular diagnosis of diseases.

SUMMARY

The invention relates to methods for determining changes to protein post-translational modifications (PTM) to classify and diagnose NAFLD. In one aspect, the invention relates to a method for treating non-alcoholic fatty liver disease (NAFLD) in a patient, comprising obtaining a capillary isoelectric focusing (cIEF) profile of a tissue sample obtained from a patient with NAFLD; wherein the cIEF profile includes isoelectric point information for one or more proteins, wherein the one or more proteins are components of a metabolic pathway related to an NAFLD pathology; identifying a protein with isoelectric point information that deviates from "normal" (an aPTM protein); selecting a therapeutic agent that targets the metabolic pathway that includes the aPTM protein; and administering an effective amount of said therapeutic agent to said patient with NAFLD. The proteins may be selected from the group consisting of Akt, ERK1/2, ChREPBP, PFK1, EHHADH, LCAD, LCAT, and HMGCS2. The metabolic pathway may be selected from the group consisting of gluconeogenesis, lipogenesis, insulin signaling, cell growth and differentiation, glycogen biosynthesis, glycolysis, peroxisomal very long chain fatty acid β-oxidation, mitochondrial long-chain fatty acid β-oxidation, ketogenesis, cholesterol biosynthesis, and long-chain fatty acid transport.

In another aspect, the invention relates to a method for determining the prognosis of non-alcoholic fatty liver disease (NAFLD) in a patient, comprising obtaining a capillary isoelectric focusing (cIEF) profile of a tissue sample obtained from a patient with NAFLD; wherein the cIEF profile includes isoelectric point information for one or more proteins that is in a metabolic pathway related to an NAFLD pathology; comparing the cIEF profile to cIEF profiles from NAFLD patients with known disease progression, and determining the prognosis based on the closest cIEF profile match. The proteins may be selected from the group consisting of Akt, ERK1/2, ChREPBP, PFK1, EHHADH, LCAD, LCAT, and HMGCS2. The metabolic pathway may be selected from the group consisting of gluconeogenesis, lipogenesis, insulin signaling, cell growth and differentiation, glycogen biosynthesis, glycolysis, peroxisomal very long chain fatty acid β-oxidation, mitochondrial long-chain fatty acid β-oxidation, ketogenesis, cholesterol biosynthesis, and long-chain fatty acid transport.

BRIEF DESCRIPTION OF THE DRAWINGS

To understand the present disclosure, it will now be described by way of example, with reference to the accompanying drawings in which embodiments of the disclosures are illustrated and, together with the descriptions below, serve to explain the principles of the disclosure.

FIG. 1 shows an assessment of hepatic steatosis with CARS microscopy. The panel of images is a comparison of CARS imaging of membrane lipids and lipid droplets (LD, white). $CH_2$ symmetric stretch vibration at 2851 $cm^{-1}$ was used. Liver tissues of C57BL/6J mice were mostly LD-free. In contrast, LD accumulation was observed in liver tissues of C57BL/6J+LD (mild microvesicular steatosis), UPase1-TG (microvesicular steatosis), C57BL/6J+F (severe microvesicular steatosis), and C57BL/6J+HFD (macrovesicular steatosis).

FIGS. 2A-2F shows PTM profiles of GSK3β as a function of fatty liver tissues. FIGS. 2A-2C are overlays of capillary isoelectric focusing (cIEF) electropherograms of GSK3β in the liver tissues of C57BL/6J versus C57BL/6J+LD (FIG. 2A), UPase1-TG (FIG. 2B), and C57BL/6J+F (FIG. 2C). FIG. 2D is an overlay of cIEF electropherograms of GSK3β in the liver tissues of C57BL/6J+LD versus C57BL/6J+HFD. FIG. 2E shows cIEF electropherograms of recombinant GSK3β probed with antibodies against GSK3β, phosphorylated GSK3β (p-GSK3β, and acetylated lysine residue (Ac-GSK3β. FIG. 2F shows the quantitative area under the curve analysis of acetylated GSK3β isoform as a function of liver tissues. Error bars are standard deviation values across 9 measurements. * and ** indicate p-value <0.01 versus C57BL/6J and C57BL/6J+LD, respectively. Chemiluminescence was normalized to 1 at pI 9.3.

FIGS. 3A-3F show PTM profiles of FABP1 as a function of fatty liver tissue. FIGS. 3A-3C are overlays of cIEF electropherograms of FABP1 in the liver tissues of C57BL/6J versus C57BL/6J+LD (FIG. 3A), UPase1-TG (FIG. 3B), and C57BL/6J+F (FIG. 3C). FIG. 3D is an overlay of cIEF electropherograms of FABP1 in the liver tissues of C57BL/6J+LD versus C57BL/6J+HFD. FIG. 3E is IEF electropherogram of recombinant of recombinant FABP1 probed with antibodies against FABP1, phosphorylated threonine residue (pThr-FABP1), and acetylated lysine residue (Ac-FABP1). FIG. 3F shows the quantitative area under the curve analysis of combined acetylated and phosphorylated FABP1 isoforms as a function of liver tissues. Error bars are standard deviation values across 9 measurements. * and ** indicate p-value <0.01 versus C57BL/6J and C57BL/6J+LD, respectively. Chemiluminescence was normalized to 1 at pI 9.2.

FIGS. 4A-4F show PTM profiles of FABP5 as a function of fatty liver tissues. FIGS. 4A-4C are overlays of cIEF electropherograms of FABP5 in the liver tissues of C57BL/6J versus C57BL/6J+LD (FIG. 4A), Upase1-TG (FIG. 4B), and C57BL/6J+F (FIG. 4C). FIG. 4D is an overlay of cIEF electropherograms of FABP5 in the liver tissues of C57BL/6J+LD versus C57BL/6J+HFD. FIG. 4E is cIEF electropherograms of recombinant FABP5 and recombinant FABP5 treated with λ phosphatase. FIG. 4F shows the quantitative area under the curve analysis of phosphorylated FABP5 isoform as a function of liver tissues. Error bars are standard deviation values across 9 measurements. * and ** indicate p-value <0.01 versus C57BL/6J and C57BL/6J+LD, respectively. Chemiluminescence was normalized to 1 at pI 5.6.

FIG. 5A show the PTM profile of FOXO1 as a function of fatty liver tissues. FIGS. 5A-5C are overlays of cIEF electrograms of FOXO1 in the liver tissues of C57BL/6J versus C57BL/6J+LD (FIG. 5A), UPase1-TG (FIG. 5B), and C57BL/6J+F (FIG. 5C). FIG. 5D is an overlay of cIEF electropherograms of FOXO1 in the liver tissues of C57BL/6J+LD versus C57BL/6J+HFD. FIG. 5E is cIEF electropherograms of recombinant FOXO1 probed with antibodies against FOXO1, acetylated lysine residue, and phosphorylated tyrosine and threonine residues. FIG. 5F shows the quantitative area under the curve analysis of glycosylated FOXO1 isoform as a function of liver tissues. Error bars are standard deviation values across 9 measurements. ** indicates p-value <0.01 versus C57BL/6J+LD. Peak chemiluminescence was normalized to 1.

FIGS. 6A-6E show detection of FOXO1 glycosylation with 2D Western blot and cIEF immunoassays. FIG. 6A shows a Western blot with anti-FLAG antibodies of HepG2 cells without and with transfection with a plasmid that constitutively express FLAG-tagged FOXO1. FIG. 6B is a graph showing treatment with PUGNAc, an inhibitor of O-GlcNAc-β-N-acetylglucosaminidase, increases the O-linked glycosylation profile in total protein extract of HepG2 cells. FIG. 6C shows treatment with glucosamine, which is known to induce FOXO1 glycosylation, causes a shift to FLAG-tagged FOXO1 toward basic pI values on a 2D Western blot. FIG. 6D is an overlay of IEF electropherograms of HepG2 cells and HepG2 cells treated with PUGNAc. FIG. 6E is an overlay of IEF electropherograms of HepG2 cells and HepG2 cells treated with glucosamine. Peak chemiluminescence was normalized to 1 in FIG. 6B and FIG. 6E.

FIGS. 7A-7F show the PTM profile of EHHADH as a function of fatty liver tissues. FIGS. 7A-7C are overlays of cIEF electropherograms of EHHADH in the liver tissues of C57BL/6J versus C57BL/6J+LD (FIG. 7A), UPase1-TG (FIG. 7B), and C57BL/6J+F (FIG. 7C). FIG. 7D is an overlay of cIEF electropherograms of EHHADH in the liver tissues of C57BL/6J+LD versus C57BL/6J+HFD. FIG. 7E are cIEF electropherograms of recombinant EHHADH probed with antibodies against EHHADH, phosphorylated threonine and tyrosine residues, and acetylated lysine residue. FIG. 7F shows the quantitative area under the curve analysis of combined acetylated and phosphorylated EHHADH isoform as a function of liver tissues. Error bars are standard deviation values across 9 measurements. * indicates p-value <0.01 versus C57BL/6J. Peak chemiluminescence was normalized to 1.

FIGS. 8A-8F show the PTM profile of PFK1 as a function of fatty liver tissues. FIGS. 8A-8C are overlays of cIEF electropherograms of PFK1 in the liver tissues of C57BL/6J versus C57BL/6J+LD (FIG. 8A), UPase1-TG (FIG. 8B), and C57BL/6J+HFD (FIG. 8C). FIG. 8D show an overlay of cIEF electropherograms of PFK1 in the liver tissues of C57BL/6J+LD versus C57BL/6J+HFD. FIG. 8E are cIEF electropherograms of C57BL/6J liver tissue extracts without and with treatment with λ phosphatase and probed with antibodies against PFK1. FIG. 8F shows the quantitative area under the curve analysis of phosphorylated PFK1 isoform as a function of liver tissues. Error bars are standard deviation values across 9 measurements. * indicates p-value <0.01 versus C57BL/6J. Peak chemiluminescence was normalized to 1.

FIGS. 9A-8H show the PTM profile of LCAT as a function of fatty liver tissues. FIGS. 9A-9C are overlays of cIEF electropherograms of LCAT in the liver tissues of C57BL/6J versus C57BL/6J+LD (FIG. 9A), UPase1-TG (FIG. 9B), and C57BL/6J+F (FIG. 9C). FIG. 9D shows an overlay of cIEF electropherograms of PFK1 in the liver tissues of C57BL/6J+LD versus C57BL/6J+HFD. FIG. 9E are cIEF electropherograms of recombinant LCAT probed with antibodies against LCAT and phosphorylated serine residue. FIG. 9F are cIEF electropherograms of C57BL/6J+HFD liver tissue extracts without and with deglycosylases treatment and probed with antibodies against LCAT. FIGS. 9G and 9H show the quantitative area under the curve analysis of phosphorylated (FIG. 9G) and glycosylated (FIG. 9H) LCAT isoform as a function of liver tissues. Error bars are standard deviation values across 9 measurements. * and ** indicate p-value <0.01 versus C57BL/6J and C57BL/6J+LD, respectively. Chemiluminescence was normalized to 1 at pI 5.8.

FIGS. 10A-10F show the PTM profile of HMGCS2 as a function of fatty liver tissues. FIGS. 10A-10C are overlays of cIEF electropherograms of HMGCS2 in the liver tissues of C57BL/6J versus C57BL/6J+LD (FIG. 10A), UPase1-TG (FIG. 10B), and C57BL/6J+F (FIG. 10C). FIG. 10D shows an overlay of cIEF electropherograms of HMGCS2 in the liver tissues of C57BL/6J+LD versus C57BL/6J+HFD. FIG. 10E are cIEF electropherograms of recombinant HMGCS2 probed with antibodies against HMGCS2, phosphorylated threonine, and acetylated lysine residue. FIG. 10F shows quantitative area under the curve analysis of combined acetylated and phosphorylated HMGCS2 isoform as a function of liver tissues. Error bars are standard deviation values across 9 measurements. * indicates p-value <0.01 versus C57BL/6J. Chemiluminescence was normalized to 1 at pI 7.5.

FIGS. 11A-11F show the PTM profile of ChREBP as a function of fatty liver tissues. FIGS. 11A-11C are overlays of cIEF electropherograms of ChREBP in the liver tissues of C57BL/6J versus C57BL/6J+LD (FIG. 11A), UPase1-TG (FIG. 11B), and C57BL/6J+F (FIG. 11C). FIG. 11D shows an overlay of cIEF electropherograms of ChREBP in the liver tissues of C57BL/6J+LD versus C57BL/6J+HFD. FIG. 11E shows cIEF electropherograms of C57BL/6J+LD liver tissue extracts without and with treatment with λ phosphatase and probed with antibodies against ChREBP. FIG. 11F shows the quantitative area under the curve analysis of phosphorylated ChREBP isoform as a function of liver tissues. Error bars are standard deviation across 9 measurements. * and ** indicate p-value <0.01 versus C57BL/6J and C57BL/6J+LD, respectively. Chemiluminescence was normalized to 1 at pI 8.4.

FIGS. 12A-12H show the PTM profiles of LCAD as a function of fatty liver tissues. FIGS. 12A-12C are overlays of cIEF electropherograms of LCAD in the liver tissues of C57BL/6J versus C57BL/6J+LD (FIG. 12A), UPase1-TG (FIG. 12B), and C57BL/6J+F (FIG. 12C). FIG. 12D is an overlay of cIEF electropherograms of LCAD in the liver tissues of C57BL/6J+LD versus C57BL/6J+HFD. FIG. 12E show cIEF electropherograms of C57BL/6J+F liver tissue extracts without and with treatment with deglycosylases and probed with antibodies against LCAD isoform as a function of liver tissues. FIG. 12F shows the quantitative area under the curve analysis of glycosylated LCAD isoform as a function of liver tissues. FIG. 12G are cIEF electropherograms of a recombinant CLAD probed with antibodies against acetylated lysine residues. FIG. 12H shows the quantitative area under the curve analysis of acetylated LCAD isoform as a function of liver tissues. Error bars are standard deviation values across 9 measurements. * and ** indicate p-value <0.01 versus C57BL/6J and C57BL/6J+LD, respectively. Chemiluminescence was normalized to 1 at pI 6.4.

FIGS. 13A-13E show the PTM profile of Akt as a function of fatty liver tissue. FIGS. 13A-13C are overlays of cIEF electropherograms of Akt in the liver tissues of C57BL/6J versus C57BL/6J+LD (FIG. 13A), UPase1-TG (FIG. 13B), and C57BL/6J+F (FIG. 13C). FIG. 13D is an overlay of cIEF electropherograms of Akt in the liver tissues of C57BL/6J+LD versus C57BL/6J+HFD. FIG. 13E shows the quantitative area under the curve analysis of phosphorylated Akt isoform as a function of liver tissues. Error bars are standard deviation values across 9 measurements. * and ** indicate p-value <0.01 versus C57BL/6J and C57BL/6J+LD, respectively. Chemiluminesence was normalized to 1 at pI 6.1.

FIGS. 14A-14E show the PTM profile of ERK1/2 as a function of fatty liver tissue. FIGS. 14A-14C are overlays of cIEF electropherograms of ERK1/2 in the liver tissues of C57BL/6J versus C57BL/6J+LD (FIG. 14A), UPase1-TG (FIG. 14B), and C57BL/6J+F (FIG. 14C). FIG. 14D is an overlay of cIEF electropherograms of ERK1/2 in the liver tissues of C57BL/6J+LD versus C57BL/6J+HFD. FIG. 14E shows the quantitative area under the curve analysis of phosphorylated ERK1/2 isoform as a function of liver tissues. Error bars are standard deviation values across 9 measurements. * and ** indicate p-value <0.01 versus C57BL/6J and C57BL/6J+LD, respectively. Chemiluminesence was normalized to 1 at pI 6.6.

DETAILED DESCRIPTION

The present invention relates generally to methods for classifying fatty liver by profiling protein post-translational modifications (PTM). More particularly, the present invention is directed to methods of using high-throughput capillary isoelectric focusing (cIEF) immunoassays to determine NAFLD disease progression, prognosis, and appropriate treatment.

The inventor has discovered NAFLD is a heterogeneous disease and that NAFLD patients can be classified based on post-translational modifications of certain proteins. The different classes differ in the metabolic and signaling pathways that are perturbed to create disease and also display different disease progressing responses to treatment. Thus, the classification of NAFLD patients disclosed herein can be used to predict outcomes and determine appropriate treatment of NAFLD patients.

Understanding the causes of fatty liver is critical for the development of effective therapeutic intervention. Changes to the PTM of liver proteins may be due to distinct causes such as aging, genetics, drug-induced, and high-fat diets. Methods of using cIEF immunoassays to rapidly detect nutrient-sensitive protein PTM (e.g., acetylation, glycosylation, and phosphorylation) can be used to identify the affected metabolic pathway, where the protein plays a critical function. cIEF immunoassays may be used to profile PTM of metabolic and signaling proteins in individual NAFLD patients using samples from tissue biopsies.

Abnormal protein PTM (aPTM) is often associated with impaired liver nutrient sensing and metabolic signaling. Thus, changes in the protein PTM of a panel of 12 proteins may serve as diagnostic markers to evaluate affected pathways in fatty liver tissues, such as gluconeogenesis (FOXO1), lipogenesis (ChREBP), insulin signalling (Akt), cell growth and differentiation (ERK1/2), glycogen biosynthesis (GSK3β), glycolysis (ChREBP and PFK1), peroxisomal very-long-chain fatty acid β-oxidation (EHHADH), mitochondrial long-chain fatty acid β-oxidation (LCAD), ketogenesis (HMGCS2), cholesterol biosynthesis (LCAT), and long-chain fatty acid transport (FABP1 and FABP5).

In one aspect, the invention relates to methods of treating non-alcoholic fatty liver disease (NAFLD) in a patient by obtaining a capillary isoelectric focusing (cIEF) profile of a tissue sample obtained from a patient with NAFLD; wherein the cIEF profile includes isoelectric point information for one or more proteins, wherein the one or more proteins are components of a metabolic pathway related to an NAFLD pathology; identifying a protein with isoelectric point information that deviates from "normal" (an aPTM protein);

selecting a therapeutic agent that targets the metabolic pathway that includes the aPTM protein; and administering an effective amount of the therapeutic agent to said patient with NAFLD.

The therapeutic agent may be, for example, a FOXO1 inhibitor, a ChREBP inhibitor, an Akt inhibitor, an ERK1/2 inhibitor, a GSK3β inhibitor, a PFK1 inhibitor, an EHHADH inhibitor, a LCAD inhibitor, a HMGCS2 inhibitor, an LCAT inhibitor, a FABP1 inhibitor, a FABP5 inhibitor, or a combination thereof. The therapeutic agent may also be any molecule capable of modifying protein PTM profile such as an inhibitor of kinases, deglycosylases, and deacetylases, or a donor substrate capable of changing cellular concentrations of ATP, acetyl-CoA, or O-GlcNAc, or any combination thereof.

In another aspect, the invention relates to methods for determining the prognosis of non-alcoholic fatty liver disease (NAFLD) in a patient by obtaining a capillary isoelectric focusing (cIEF) profile of a tissue sample obtained from a patient with NAFLD; wherein the cIEF profile includes isoelectric point information for one or more proteins that is in a metabolic pathway related to an NAFLD pathology; and comparing the cIEF profile to cIEF profiles from NAFLD patients with known disease progression, and determining the prognosis based on the closest cIEF profile match. In some instances, the condition may not progress beyond simple fatty liver or NASH. Depending on the cause of the condition (e.g., obesity, diabetes, etc.) the disease may reverse and even go away after treatment including weight loss (if obesity is the cause), or with good control of diabetes (if diabetes is the cause). In some instances, fatty liver may progress to NASH in some patients, and NASH may progress to cirrhosis in some patients. Cirrhosis is very serious, can lead to liver failure and be fatal. Thus, the need for treatment with a therapeutic agent can be determined based on a patient's prognosis. It is difficult to distinguish the cause of the patient's fatty liver using standard of care methods. Hence, it is difficult for physicians to determine the treatment choice as the patients' prognosis is uncertain. In view of this problem, a method for prognosis in NAFLD patients which guides the treatment decisions is highly desirable In one embodiment, fatty liver may be classified by changes to the nutrient-sensitive PTM profiles of liver protein and the affected metabolic pathways may be identified. Changes to the nutrient-sensitive PTM profiles may include, for example, acetylation of GSK3β at Lys205, deacetylation of GSK3β by Sirt1, increased phosphorylation of glycogen synthase (GS), inhibition of GS enzymatic activity, suppression of acetylated GSK3β isoform in the liver tissues, or reduction of hepatic glycogen content following fenofibrate treatment.

In another embodiment, PTM affects the function of FABP isoforms. Fatty acid transfer between an intestinal fatty acid binding protein (FABP2) and the phospholipid membrane may be impaired following the acetylation of FABP2. Electrostatic interaction between phospholipid membrane and protein surface is critical for fatty acid transfer. Acetylation of lysine residues removes the surface positive charges and reduces fatty acid transfer efficiency. Similarly, increased acetylation of FABP1 in the fatty liver tissues may be associated with impaired fatty acid transport.

In another embodiment, the PTM profile of FOXO1 may be used as an indicator of hepatic glucose production. FOXO1 can mediate insulin-regulated suppression of hepatic gluconeogenesis through, for example, Akt phosphorylation or interaction with PGC-1α. O-linked glycosylation of FOXO1 can promote hepatic gluconeogenesis by activating the expression of phosphoenolpyruvate and glucose-6-phosphate in the absence of insulin stimulation.

Generally the patient is human, although the patient may be an animal, including mammals such as rodents (including mice, rats, hamsters and guinea pigs), cats, dogs, rabbits, farm animals including cows, horses, goats, sheep, pigs, and primates (including monkeys, chimpanzees, orangutans and gorillas).

The content of each of the patents, patent applications, patent publications and published articles cited in this specification are herein incorporated by reference in their entirety.

The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLES

Animal Models
Mouse strains are summarized in Table 1.

TABLE 1

Animal models of fatty liver

| Mouse model | Description | Age (weeks) | Fatty liver classification | Cause of fatty liver |
|---|---|---|---|---|
| C57BL/6J | Control, male | 10-12 | No steatosis | Not applicable |
| C57BL/6J + LD | Lean diet for 16 weeks | 26-28 | Microvesicular steatosis | Ageing |
| UPase1-TG | Overexpression of UPase1 | 10-12 | Microvesicular steatosis | Genetic mutation |
| C57BL/6J + F | Fenofibrate diet for 5 days | 11-13 | Microvesicular steatosis | Drug-induced |
| C57BL/6J + HFD | High-fat diet for 16 | 26-28 | Macrovesicular steatosis | High-fat diet |

C57BL/6 J and UPase1-TG mice were fed a lean diet that provides 4.6 kcal/g (22% by calorific value from fat, 23% from protein, and 55% from carbohydrates; PicoLab Mouse Diet, Catalog No 5058, LabDiet, Brentwood, Mo., USA). C57BL/6 J+LD mice were fed a lean diet for 16 weeks. C57BL/6 J+F mice were fed a lean diet supplemented with fenofibrate (400 mg/kg per day) for 5 days. C57BL/6 J+HFD mice were fed a high-fat diet that provides 5.24 kcal/g (60% from fat, 20% from protein, and 20% from carbohydrates) for 16 weeks (Catalog No D12492, Research Diets Inc, New Brunswick, N.J., USA). C57BL/6 J mice served as a control for C57BL/6 J+LD, UPase1-TG, and C57BL/6 J+F mice. On the other hand, C57BL/6 J+LD mice served as a control for C57BL/6 J+HFD mice. All animal studies were performed in conformity with the Public Health Service Policy on Humane Care and Use of Laboratory Animals and with the approval of the Animal Care and Use Committees at Nevada Cancer Institute, Desert Research Institute, and Touro University Nevada.

Coherent Anti-Stokes Raman Scattering (CARS) Microscopy

A custom built CARS microscope was employed to assess liver lipid content at CH2 vibrational frequency of 2851 $cm^{-1}$. Images presented were stacks of approximately 31 frames taken at 1-micron interval along the vertical axis. Liver samples from 9 mice per animal group were examined with CARS microscopy to evaluate steatosis classification.

Preparation of Liver Tissue Lysates

Approximately 500 mg of frozen liver tissues was added to 300 µl of RIPA buffer (Cat. No. 8990, Life Technologies, Grand Island, N.Y. 14702) containing proteinase and phosphatase inhibitors and homogenized twice at 6 seconds duration. Liver tissue homogenates were incubated on ice for 10 minutes, sonicated 4 times at 5 seconds duration, rotated at 4° C. for 2 hours, and centrifuged at 12000 rpm on an Eppendorf 5430R microfuge for 20 minutes at 4° C. Supernatant was collected, prepared in Premix G2 pH 5-8 separation gradient containing pI standards (Protein Simple), and used for cIEF immunoassays.

Preparation of Recombinant Proteins

Recombinant proteins were diluted in Bicine/CHAPS Lysis and Sample Diluent (Cat. No. 040-764, Protein Simple) which included DMSO inhibitor (Cat. No. 040-510, Protein Simple) and bovine serum albumin (0.5 mg/ml final concentration). Diluted proteins were mixed with Premix G2 pH3-8 (Cat. No. 040-968, Protein Simple), pI standard Ladder 1 (Cat. No. 040-644), pI standard 9.7 (Cat. No. 040-790) to 1:3 ratio, and used for cIEF immunoassays.

cIEF Immunoassays

A NanoPro 1000 cIEF system (Protein Simple, Santa Clara, Calif., USA) was employed for profiling protein PTM. Samples of 400 nl volume were separated by isoelectric focusing using the 96-capillary system, followed by immobilization of the proteins onto the inner capillary walls. Primary and secondary antibodies (Tables 2 and FIG. 6) were introduced into the capillaries, followed by chemiluminescence detection reagents. The incubation times were 110 and 55 min for primary and secondary antibodies, respectively. The separation time was 50 minutes at 15 MicroWatts. All samples were loaded in triplicate into capillaries to evaluate the consistency of capillary-to-capillary measurement. Each experiment was performed in triplicate to ensure repeatability. A minimum of nine cIEF measurements were done for each protein per animal group. On average, 40 ng of total cellular protein was loaded into each capillary. The standard exposure time during signal detection was 240 seconds.

Antibodies and Recombinant Proteins

TABLE 2

List of primary and secondary antibodies

| Antibodies | Vendor | Cat. No. | Host |
|---|---|---|---|
| Primary antibodies | | | |
| FOXO | Abcam | ab179450 | r |
| AKT | Cell Signaling | cs9272 | r |
| EHHADH | Abcam | ab93172 | r |
| GSK3β | Abcam | ab69739 | r |
| pGSK3β | Cell Signaling | cs9336 | r |
| PFK1 | Novus | NBP2-32169 | r |
| HMGCS2 | Abcam | ab137043 | r |
| FABP1 | Abcam | ab7847 | r |
| FABP5 | Abcam | ab128650 | r |
| ChREBP | Abcam | ab157153 | r |
| p-Tyr | Santa Cruz | sc-7020 | m |
| p-Thr | Santa Cruz | sc-5267 | m |
| p-Ser | Abcam | ab9332 | m |
| LCAT | Novus | NBP1-5950 | r |
| LCAD | Novus | 1-89289 | r |
| ERK | Protein Simple | 040-474 | r |
| O-GlcNAc | Abcam | ab2739 | m |
| Acetylated Lysine | Cell Signaling | cs9441 | r |
| FLAG (DDDDK) | Abcam | ab21536 | r |

TABLE 2-continued

List of primary and secondary antibodies

| Antibodies | Vendor | Cat. No. | Host |
|---|---|---|---|
| Secondary antibodies | | | |
| anti Rabbit IgG, HRP linked | Cell Signaling | cs7074 | g |
| anti mouse IgG, HRP linked | Cell Signaling | cs7076 | h |

TABLE 3

List of recombinant proteins

| Recombinant proteins | Vendor | Cat. No. |
|---|---|---|
| GSK3β | Origene (Rockville, MD) | TP300468 |
| FABP1 | Origene (Rockville, MD) | TP307592 |
| FOXO1 | Origene (Rockville, MD) | TP300477 |
| EHHADH | Origene (Rockville, MD) | TP307928 |
| HMGCS2 | Origene (Rockville, MD) | TP308128 |
| LCAT | Origene (Rockville, MD) | TP706551 |
| LCAD | Novoprotein (Summit, NJ) | C811 |

Protein Dephosphorylation with λ Phosphatase

To remove the phosphate group from liver proteins, 1 µl of λ phosphatase (Cat. No. 14-405, Merck Millipore, Billerica, Mass.) was added to 1 µl of reaction buffer (final concentrations of 5 mM DTT, 50 mM Hepes, 100 µM EDTA, 2 mM $MnCl_2$) and 8 µl of liver tissue lysates (2 mg/ml of total protein concentration). The mixture was incubated at 37° C. for 1 hour, chilled on ice to stop the reaction and then prepared for cIEF immunoassays.

Statistical Analysis

Data were presented as average value±standard deviations. Statistical analysis was performed using Excels' paired Student's t-test and analysis of variance functions for experimental versus control mice groups. Statistical significance was set at $p \leq 0.05$ versus control animal group.

Example 1

Mouse models with fatty liver induced by different causes were employed, such as ageing, genetic mutation, acute drug administration, and high-fat diet (Table 1). Young C57BL/6 J mice of approximately 3 months old served as a control. Mouse models of hepatic microvesicular steatosis were represented by C57BL/6 J mice at approximately 6 months old (ageing, C57BL/6 J+LD), C57BL/6 J mice with transgenic overexpression of uridine phosphorylase 1 (genetic mutation, UPase1-TG), and C57BL/6 J mice fed a fenofibrate-supplemented diet (drug-induced, C57BL/6 J+F) (FIG. 1). On the other hand, a mouse model of hepatic macrovesicular steatosis was represented by C57BL/6 mice fed a high-fat diet for 4 months (high-fat diet, C57BL/6 J+HFD). Classification of hepatic steatosis was performed according to standard histopathology guidelines, using both Oil Red O histology and coherent anti-Stokes Raman scattering (CARS) microscopy as described previously [35]. Hepatic steatosis in all liver tissues was pan-lobular, with no evidence of inflammation or fibrosis when analyzed with CD11b+/CD11c+ immunostaining or Masson trichrome staining, respectively. Fatty liver tissues were profiled with cIEF immunoassays to study PTM of proteins critical for liver metabolism and signaling.

PTM of glycogen synthase kinase 3β (GSK3β) was examined in normal and fatty liver tissues. GSK3β is an enzyme that regulates glycogen biosynthesis by phosphorylating and inactivating glycogen synthase. GSK3β focused around four distinctive pI values of 6.2, 8.8, 8.9, and 9.3 (FIG. 2A). After normalizing the peak value at pI 9.3 to 1 for all tissue samples, we observed that the peak intensity at pI 6.2 was slightly reduced for C57BL/6 J+LD and UPase1-TG, nearly suppressed for C57BL/6 J+F, and substantially increased for C57BL/6 J+HFD (FIGS. 2A-2D). In contrast, the peak intensities at pI 8.8 and 8.9 were nearly identical for all tissue samples. To assign pI values to GSK3β isoforms, recombinant GSK3β was probed with antibodies against GSK3β, phosphorylated GSK3β, and acetylated lysine residue (FIG. 2E). The pI value of 6.2 was due to the acetylated isoform of GSK3β, whereas the pI values of 8.8 and 8.9 were due to phosphorylated isoforms of GSK3β. The pI value of 9.3 was attributed to unmodified GSK3β. Quantitative analysis of areas under the curve revealed a more than two-fold reduction of lysine acetylation of GSK3β in C57BL/6 J+F mice compared with control mice (FIG. 2F). In contrast, lysine acetylation of GSK3β increased by nearly two-fold in C57BL/6 J+HFD mice compared with controls. GSK3β isoforms could be clearly separated based on pI values with cIEF immunoassays. Protein acetylation and phosphorylation of GSK3β caused shifts of approximately 3.1 and 0.4 towards lower pI values, respectively.

PTM of liver-specific fatty acid binding protein FABP1 was profiled in normal and fatty liver tissues. FABP1 is a protein that participates in the transport and metabolism of long-chain fatty acids. In liver tissues of C57BL/6 J, C57BL/6 J+LD, and UPase1-TG mice, FABP1 exhibited a single dominant peak with a pI value of 9.2 (FIGS. 3A and 3B). We assigned this pI value of 9.2 to the unmodified FABP1 isoform. In contrast, broad bands that spanned pI values from 5.0 to 8.3 and from 5.0 to 6.3 were observed in the liver tissues of C57BL/6 J+F and C57BL/6 J+HFD mice, respectively (FIGS. 3C and 3D). To assign pI values to FABP1 isoforms, recombinant FABP1 was probed with antibodies against FABP1, phosphorylated threonine residues, and acetylated lysine residues (FIG. 3E). Phosphorylated FABP1 exhibited a dominant peak at pI 6.3. In contrast, acetylated FABP1 exhibited two peaks, a dominant peak at pI 7.3 and a lesser peak at pI 5.6. A previous study had revealed that FABP1 was acetylated at multiple lysine residues in the liver tissues of C57BL/6 J+F mice [34]. The data suggested that FABP1 in the liver tissues of both C57BL/6 J+F and C57BL/6 J+HFD mice was modified by both phosphorylation and acetylation. The broad pI profiles of FABP1 were likely due to multiple phosphorylation and acetylation. Quantitative analysis of areas under the curve from pI 5.0 to 8.3 revealed substantial increases in PTM of FABP1 in the liver tissues of C57BL/6 J+F and C57BL/6 J+HFD mice (FIG. 3F).

PTM of an epidermal fatty acid binding protein, FABP5, was further evaluated in normal and fatty liver tissues. Like FABP1, FABP5 participates in the transport and metabolism of long-chain fatty acids. In liver tissues of C57BL/6 J, C57BL/6 J+LD, and UPase1-TG mice, FABP5 exhibited a peak at pI 5.6 and a left shoulder that centered around pI 5.5 (FIGS. 4A and 4B). On the other hand, the left shoulder was nearly suppressed in the liver tissues of C57BL/6 J+F and C57BL/6 J+HFD mice (FIGS. 4C and 4D). Treating recombinant FAPB5 with λ phosphatase completely removed the left shoulder peak (FIG. 4E). Thus, phosphorylation of FABP5 caused a 0.1 shift towards a lower pI value. FABP5 phosphorylation was clearly suppressed in the liver tissues of both C57BL/6 J+F and C57BL/6 J+HFD mice (FIG. 4F).

While protein acetylation and phosphorylation caused shifts towards acidic pI values, protein glycosylation generally caused shifts towards basic pI values. Experiments conducted in cultured HepG2 cells revealed that glycosylation of forkhead box protein 01 (FOXO1) led to distinctive right-shifted peaks (FIG. 7). FOXO1 is a transcription factor that controls the expression of proteins important for gluconeogenesis. Glycosylation of FOXO1 has been shown to promote gluconeogenesis in hepatocytes. FOXO1 glycosylation was examined in both normal and fatty liver tissues, and complex pI profiles for FOXO1 were observed, with multiple peaks that spanned from pI 5.0 to 7.5 (FIGS. 5A-5D). Using recombinant FOXO1 and antibodies against acetylated lysine and phosphorylated tyrosine and threonine residues, both phosphorylation and acetylation contributed to the complex pI profile of FOXO1 (FIG. 5E). The known PTMs of FOXO1 in the literature include ubiquitination, acetylation, phosphorylation, and glycosylation [39-41]. In the liver tissues of C57BL/6 J+HFD mice, distinctive right-shifted peaks from pI 7.5 to 9.0 were observed, which were attributed to glycosylated isoforms of FOXO1 (FIG. 5D). Quantitative analysis of areas under the curve revealed that there was a three-fold increase in glycosylated FOXO1 in the liver tissues of C57BL/6 J+HFD mice compared with control C57BL/6 J mice (FIG. 5F). Glycosylation of FOXO1 was not statistically significant in the liver tissues of other mouse models compared with control mice. Taken together, cIEF immunoassays were capable of detecting multiple modes of PTM including phosphorylation, acetylation, and glycosylation.

Using cIEF to detect and assign changes to protein PTM, the study was extended to evaluate eight additional proteins important for liver metabolism and signaling (Table 4). These include protein kinase B (Akt); extracellular signal-regulated kinases (ERK1/2); carbohydrate-responsive element-binding protein (ChREBP); phosphofructokinase 1 (PFK1); peroxisome bifunctional enzyme or enoyl-CoA, hydratase/3-hydroxyacyl CoA dehydrogenase (EHHADH); long-chain acyl CoA dehydrogenase (LCAD); lecithincholesterol acyltransferase (LCAT); and 3-hydroxy-3-methyl-glutaryl-CoA synthase 2 (HMGCS2). Due to the automated capability that permits the handling of up to 96 samples, changes to the PTM of all 12 proteins were probed in a single run using nanograms of liver tissue extracts. Data on changes to the protein PTM in fatty liver tissues are presented in FIGS. 8-14 and summarized in Table 2.

Substantial differences in protein PTM were observed among fatty liver tissues. Using changes to protein PTM as indicators of changes to nutrient sensing and metabolic signaling, affected pathways were assigned to fatty liver tissues (Table 3). A common affected pathway in all fatty liver tissues was mitochondrial fatty acid β-oxidation. In contrast, peroxisomal β-oxidation of very-long-chain fatty acids was affected only in the liver tissues of UPase1-TG and C57BL/6 J+F mice. Gluconeogenesis, lipogenesis, insulin signalling, and cell growth and proliferation were affected in the liver tissues of C57BL/6 J+LD, C57BL/6 J+F, and C57BL/6 J+HFD mice. Glycolysis was affected in the liver tissues of C57BL/6 J+LD, UPase1-TG, and C57BL/6 J+F mice. Cholesterol biosynthesis, ketogenesis, and fatty acid transport were affected in the liver tissues of C57BL/6 J+F and C57BL/6 J+HFD mice. Thus, fatty liver tissues may be classified by their protein PTM profiles and the affected metabolic and signaling pathways.

TABLE 4

List of liver proteins profiled for PTM

| Protein | Function | Metabolic Pathway | PTM | Threotical PI Values | MW (kD) | Sequence Length (aa) |
|---|---|---|---|---|---|---|
| Akt | Protein kinase | Insulin signaling | P | 5.63 | 55.7 | 480 |
| ChREBP | Transcription factor | Glycolysis & Lipogenesis | P, Gly, Ac | 7.96 | 94.9 | 864 |
| EHHADH | Dehydrogenase | Peroxisomal β-oxidation | Ac, P | 9.22 | 78.3 | 718 |
| ERK1/2 | Protein kinase | Cell growth & differentiation | P | 6.15 (ERK1), 6.50 (ERK2) | 43.1 (ERK1), 41.3 (ERK2) | 380 (ERK1), 358 (ERK2) |
| FABP1 | Transport | Fatty acid transport | Ac, P | 8.59 | 14.2 | 127 |
| FABP5 | Transport | Fatty acid transport | P | 6.5 | 15.1 | 135 |
| FOXO1 | Transcription factor | Gluconeogenesis | P, Gly, Ac | 6.6 | 69.6 | 652 |
| GSK3β | Protein kinase | Glycogen biosynthesis | P, Ac | 8.98 | 46.7 | 420 |
| HMGCS2 | Transferase | Ketogenesis | Ac | 8.65 | 56.8 | 508 |
| LCAD | Dehydrogenase | Mitochondrial β-oxidation | Ac | 6.5 | 47.9 | 430 |
| LCAT | Transferase | Cholesterol biosynthesis | P, Gly | 5.97 | 49.7 | 438 |
| PFK1 | Protein kinase | Glycolysis | Gly | 8.23 | 85.1 | 780 |

Example 2

Treatment of HepG2 Cells with PUGNAc.

HepG2 cells were maintained in DMEM media with 25 mM glucose and 10% fetal calf serum. HepG2 cells were treated for 48 hours with 100 μM PUGNAc (Cat. No. A7229, Sigma, St. Louis, Mo.). Total HepG2 cell extracts were collected and evaluated with 1D Western blots using antibodies against O-GlcNAc.

Treatment of HepG2 Cells with Glucosamine

HepG2 cells were transiently transfected with an expression vector that expressed FOXO1 with a Myc-DDK tag (Cat. No. RC200477, Origene, Rockville, Md.). Transfection reagent was purchased from Life Technologies (Lipofectamine 2000, Cat. No. 11668-019, Grand Island, N.Y. 14702). HepG2 cells were treated for 48 hours with 500 μM glucosamine Total HepG2 cell extracts were collected and evaluated with 1D and 2D Western blots using antibodies against FLAG tag.

Preparation of HepG2 Total Cell Extracts.

HepG2 cells were first lysed with M-Per lysis buffer (Pierce, Rockford, Ill., USA) in the presence of protease and phosphatase inhibitors. For cIEF immunoassays, total cell lysates were prepared in Premix G2 pH 5-8 separation gradient containing pI standards (ProteinSimple).

1D Western Blot.

HepG2 total cell extracts were analyzed on 10% SDS-polyacrylamide gel. Secondary antibodies were purchased from LI-COR (Lincoln, Nebr., Cat. No. 92668070). Immunoblots were detected with the LI-COR's Odyssey CLx imaging system.

2D Western Blot.

2D Western blots of HepG2 total protein extracts were performed by Kendrick Laboratories (Madison, Wis.). Total protein extracts was diluted with 100 ul of SDS Boiling Buffer and microdialyzed overnight using 6-8,000 MWCO membrane at 4° C. Samples were then lyophilized and redissolved to 3.33 mg/ml in diluted SDS boiling Buffer: Urea Sample Buffer before loading. A total of 500 μg of total protein extracts or 150 μl was loaded for isoeletric focusing. Carrier ampholine method of isoelectric focusing was carried out in a glass tube of inner diameter 3.3 mm using 2.0% pH 4-8 mix Servalytes (Serva, Heidelberg, Germany) for 20,000 volt-hrs. After equilibration for 10 minutes in 10% glycerol, 50 mM dithiothreitol, 2.3% SDS and 0.0625 M tris, pH 6.8, each tube gel was sealed to the top of a stacking gel that overlaid a 10% acrylamide slab gel. SDS slab gel electrophoresis was carried out for about 5 hours at 25 mA/gel. After slab gel electrophoresis, the gels were placed in transfer buffer (10 mM CAPS, pH 11.0, 10% MeoH) and transblotted onto a PVDF membrane overnight at 225 mA and approximately 100 volts/two gels. The following proteins (Sigma Chemical Co., St. Louis, Mo. and EMD Millipore, Billerica, Mass.) were used as molecular mass standards: myosin (220,000), phosphorylase A (94,000), catalase (60,000), actin (43,000) carbonic anhydrase (29,000) and lysozyme (14,000). The blots were wet in 100% methanol, rinsed briefly in Tween-20 tris buffered saline (TTBS), and blocked for two hours in 5% Non Fat Dry Milk in TTBS. The blots were then incubated in primary antibody against the FLAG tag overnight and rinsed 3×10 minutes in TTBS. The blots were then placed in secondary antibody (Cat. No. NA931V, GE, Pittsburgh, Pa.) for two hours, rinsed in TTBS, treated with ECL, and exposed to X-ray film.

Treatment of liver tissue lysates with deglycosylation mix. Deglycosylation enzyme mix was purchased New England BioLabs (Cat. No. P6039S, Ipswich, Mass.) which included the following enzymes O-glycosidase, peptide: N-glycosidase F, neuraminidase, β1-4 Galactosidase, and β-N-acetylglucosaminidase. Deglycosylation was performed following manufacturer's protocols under non-denaturing reaction condition using 100 μg of liver total protein extracts.

Detecting FOXO1 Glycosylation with cIEF Immunoassays

Glycosylation of FOXO1 regulates its nucleus translocation, stability, and transcriptional activity. To stabilize glycosylated form of FOXO1, we treated HepG2 cells with PUGNAc, which inhibits O-GlcNAc-β-N-acetylglucosaminidase, the enzyme which removes O-GlcNAc from glycosylated proteins. In general, treatment with PUGNAc increased overall protein O-linked glycosylation profiles of HepG2 total cell extract (FIG. 6A). Using cIEF immunoassays to measure the pI distribution of FOXO1, PUGNAc treatment induced a new FOXO1 peak that centered at pI 8.25 (FIG. 6B). To confirm that the shift toward a basic pI value was due to glycosylation of FOXO1, HepG2 cells were transfected with a plasmid that constitutively expressed FLAG-tagged FOXO1 (FIG. 6C). Then, HepG2 cells were treated with glucosamine to induce FOXO1 glycosylation (2). 2D Western blots were performed using primary antibodies against the FLAG tag. FLAG-tagged FOXO1 HepG2 cells treated with glucosamine exhibited an additional gel spot at a basic pI value (FIG. 6D) compared to untreated control HepG2 cells. Consistently cIEF immunoassays revealed the presence of peaks at pI>7.5. Taken together, we concluded that FOXO1 peaks at pI values greater than 7.5 in a cIEF electropherogram were due to protein glycosylation.

Detecting PTM of EHHADH with cIEF Immunoassays

Enoyl-CoA, Hydratase/3-Hydroxyacyl CoA Dehydrogenase or EHHADH is a bifunctional enzyme that participates in the peroxisomal β-oxidation of very long chain fatty acids. Acetylation of EHHADH has been shown to modulate its enzymatic activity. Increased acetylation of EHHADH has been reported in the liver tissues of mouse models of alcohol-induced liver injury and fenofibrate-induced fatty liver. Using cIEF immunoassays, the PTM profile of EHHADH was examined as a function of fatty liver tissues (FIGS. 7A-7D). Complex pI profiles for EHHADH with multiple broad peaks were reported. The pI profiles are consistent and reproducible within the same fatty liver tissue type. Significant changes were observed in the liver tissues of UPase1-TG and C57BL/6J+F mice compared to control C57BL/6J mice, where the pI profiles for EHHADH shifted toward the acidic values. To assign pI values to types of PTM, recombinant EHHADH was used and probed with antibodies against EHHADH, phosphorylated threonine and tyrosine residues, and acetylated lysine residues (FIG. 7E). Recombinant EHHADH exhibited a dominant peak at pI 9.9. Both phosphorylated threonine and tyrosine isoforms of EHHADH exhibited strong peaks at pI 6.3. An observable peak with weak signal-to-noise ratio at pI 5.6 was observed with acetylated lysine isoform of EHHADH. This pI 5.6 peak was also present in the electropherograms of recombinant EHHADH and phosphorylated isoforms. Weak signal-to-noise intensity for pI 5.6 peak could be attributed to low acetylation level of recombinant EHHADH. Both phosphorylation and acetylation were attributed as the PTM for EHHADH with pI values from 3.0-7.0. Quantitative analysis of areas under the curve revealed substantial increases of EHHADH phosphorylation and acetylation in the liver tissues of UPase1-TG and C57BL/6J+F mice compared to control C57BL/6J mice. No statistically significant changes in the PTM profile of EHHADH were detected in the liver tissues of C57BL/6J+LD mice compare to control C57BL/6J mice or C57BL/6J+HFD mice compared to C57BL/6J+LD mice.

Detecting PTM of PFK1 with cIE Immunoassays

Phosphofructokinase-1 (PFK-1) catalyzes a committed step in glycolysis, or the breakdown of glucose, by converting fructose-6-phosphate and ATP to fructose-1, 6-phosphate and ADP. cIEF immunoassays revealed the distribution of PFK-1 around two pI values of 6.9 and 7.3 of equal peak intensity for the liver tissues of C57BL/6J mice (FIG. 8A). After normalization to 1 for peak intensity at pI 7.3, significant reduction of peak intensity at pI 6.9 was observed for C57BL/6J+LD and UPase1-TG mice compared to C57BL/6J mice (FIG. 8A, 8B). Strikingly, peak intensity at pI 6.9 for C57BL/6J+F mice was nearly suppressed (FIG. 8C). No significant difference was observed in peak intensity at pI 6.9 between C57BL/6J+LD and between C57BL/6J+LD and C57BL/6J+HFD mice (FIG. 8D). Following the treatment of the liver tissue extracts of C57BL/6J mice with phosphatase, a substantial reduction in peak intensity at pI 6.9 and the appearance of left shoulders for the pI 7.3 peaks was observed (FIG. 8E). These observations supported the assignment of pI 6.9 peak to phosphorylated isoform of PFK-1. Quantitative analysis of areas under the curve revealed reduction of phosphorylated PFK-1 isoform by approximately 2 folds for C57BL/6J+LD and UPase1-TG mice and 10 folds for C57BL/6J+F mice compared to control C57BL/6J mice (FIG. 8F). There was no statistical different in phosphorylated PFK-1 isoform in the liver tissues of C57BL/6J+HFD mice compared to C57BL/6J+LD mice.

Detecting PTM of LCAT with cIEF Immunoassays

Lecithin-cholesterol acyltransferase (LCAT) catalyzes the conversion of free cholesterol into cholesterol ester, which forms the core of a lipoprotein particle. cIEF immunoassays revealed the distribution of LCAT around three pI values of 5.8, 6.9, and 7.3 for the liver tissues of C57BL/6J, C57BL/6J+LD, and UPase1-TG mice (FIG. 9A, 9B). In the liver tissues of C57BL/6J+F mice, LCAT was observed at a single pI value of 5.8 (FIG. 9C). However, LCAT was observed at four distinctive pI values of 5.0, 5.7, 6.9, and 7.3 in the liver tissues of C57BL/6J+HFD mice (FIG. 9D). When recombinant LCAT was probed with antibodies against phosphorylated serine residue, a single broad peak that spanned pI 4.5-6.5 was observed (FIG. 9E). This observation suggested that the new pI 5.0 and 5.7 (a slight left shift of the 5.8 peak) peaks represent the phosphorylated isoforms of LCAT. Treatment with deglycosylases caused an increase of LCAT pI 6.9 peak, coupled with a decrease of pI 7.3 peak, in the liver tissues of C57BL/6J+HFD (FIG. 9F). Based on these observations, the pI 6.9 and 7.3 peaks were assigned as glycosylated isoforms of LCAT. Quantitative analysis of areas under the curve revealed an increase of more than 5 folds in phosphorylated LCAT isoform in the liver tissues of C57BL/6J+HFD mice compared to control C57BL/6J mice (FIG. 9G). In contrast, glycosylated LCAT isoforms were nearly 10 folds lower in the liver tissues of C57BL/6J+F mice compared to C57BL/6J mice (FIG. 9H).

Detecting PTM of HMGCS2 with cIEF Immunoassays 3-hydroxy-3-methylglutaryl-CoA synthase 2 (HMGCS2) catalyzes the first reaction in ketogenesis, where acetoacetyl-CoA and acetyl-CoA combine to β-hydroxy-β-methylglutaryl-CoA (HMG-CoA). cIEF immunoassays revealed very complex pI profiles for HMGCS2 in all liver tissues (FIG. 10A-10D). A striking difference in the pI profiles for HMGCS2 was observed between the liver tissues of C57BL/6J+HFD versus C57BL/6J+LD mice. There were substantial increases in the intensity of HMGCS2 peaks at pI 6.0 and 6.3 in the liver tissues of C57BL/6J+HFD compared to C57BL/6J+LD mice (FIG. 10D). These two HMGCS2 peaks also increased in the liver tissues of C57BL/6J+F compared to C57BL/6J mice (FIG. 10C). Recombinant HMGCS2 exhibited a less complex pI profile compared to HMGCS2 of the liver tissues (FIG. 10E). Both phosphorylated and acetylated isoforms of HMGCS2 were detected with antibodies against phosphorylated threonine residues and acetylated lysine residues at pI 7.4 and 7.3, respectively. Combined phosphorylation and acetylation of a protein at multiple sites could lead to significant shifts toward acidic pI values. Thus, changes to the PTM profile of HMGCS2 were assigned as due to the both phosphorylation and acetylation. Quantitative analysis of areas under the curve from pI 5.7 to 6.4 revealed a PTM increase for HMGCS2 by 2 folds in the liver tissues of C57BL/6J+F mice versus C57BL/6J mice (FIG. 10F). A PTM increase for HMGCS2 by 3.5 folds was observed in the liver tissues of C57BL/6J+HFD mice versus C57BL/6J+LD mice.

Detecting PTM of ChREBP with cIEF Immunoassays

Carbohydrate-responsive element-binding protein (ChREBP) is a transcription factor that regulates the expression of enzymes in the glucose and lipid metabolism pathways. PTM of ChREBP controls its cellular localization and function. cIEF immunoassays revealed a complex pI profile for ChREBP that spans pI 7.2-8.7 (FIG. 11A-11D). Compared to control C57BL/6J mice, the pI profile for ChREBP of C57BL/6J+LD mice exhibited an increase in intensity from pI 7.2-8.0 (FIG. 11A). The pI profile for ChREBP of UPase1-TG mice was nearly identical with that of C57BL/6J control mice (FIG. 11B). Interestingly, the pI profile for ChREBP of C57BL/6J+F mice was substantially reduced from pI 7.2 to 8.2 compared to control C57BL/6J mice (FIG. 11C). The pI profile for ChREBP of C57BL/6J+HFD mice was also lower compared to C57BL/6J+LD from pI 7.2 to 8.2 (FIG. 11D). Following the treatment with 2 phosphatase, the pI profile from 7.2 to 8.2 for ChREBP of C57BL/6J+LD mice exhibited substantial reduction (FIG. 11E). Therefore, pI values from 7.2 to 8.2 were assigned to phosphorylated isoforms of ChREBP. Compared to control C57BL/6J mice, C57BL/6J+LD and C57BL/6J+F mice exhibited a 30% increase and a 60% reduction of phosphorylated ChREBP isoforms, respectively (FIG. 11F).

Detecting PTM of LCAD with cIEF Immunoassays

Long chain acyl-CoA dehydrogenase (LCAD) catalyzes mitochondrial fatty acid β-oxidation by forming a C2-C3 double bond on the hydrocarbon chain. PTM of LCAD has been shown to modulate its enzymatic activity. cIEF immunoassays revealed a complex pI profile for LCAD with a broad peak that spanned pI 5.5 to 6.5 and an additional narrow peak that centered at pI 6.9 (FIG. 12A-12C). The LCAD broad peak exhibited higher intensity in C57BL/6J+LD, UPase1-TG, and C57BL/6J+F mice compared to control C57BL/6J mice. The LCAD broad peak was lower in C57BL/6J+HFD mice compared to C57BL/6J+LD (FIG. 12D). The intensity of the LCAD narrow peak was the same for C57BL/6J, C57BL/6J+LD, and UPase1-TG mice (FIG. 12A, 12B). The intensity of the LCAD narrow peak was significantly higher in C57BL/6J+F mice compared to control C57BL/6J mice (FIG. 12C). In contrast, the LCAD narrow peak was nearly suppressed in C57BL/6J+HFD mice compared to C57BL/6J+LD mice (FIG. 12D). Following the treatment with deglycosylases of liver tissue extracts of C57BL/6J+F mice, the LCAD narrow peak was nearly suppressed (FIG. 12E). This peak at pI 6.9 was assigned to glycosylated LCAD isoforms. When recombinant LCAD was probed with antibodies against acetylated lysine residue, a single peak at pI 6.2 was observed (FIG. 12F). Acetylation of LCAD has also been previously reported. Thus, the broad peak was assigned to acetylated LCAD isoforms. Quantitative analysis of areas under the curve revealed 2 folds higher in glycosylated LCAD isoform in C57BL/6J+F mice than control C57BL/6J mice (FIG. 12G). In contrast, glycosylated LCAD isoform was 4 folds lower in C57BL/6J+HFD mice than C57BL/6J+LD mice. Compared to C57BL/6J mice, the level of acetylated LCAD isoform was higher in C57BL/6J+LD, UPase1-TG, and C57BL/6J+HFD mice (FIG. 12H). For C57BL/6J+HFD mice, the level of acetylated LCAD isoform was approximately 30% lower than C57BL/6J+LD mice.

Detecting Changes in the Phosphorylation Profile of Akt with cIEF Immunoassays.

Protein kinase B (Akt) is a serine/threonine protein kinase that participates in the insulin signaling pathway, glucose metabolism, and multiple other cellular processes. Phosphorylation of Akt generally activates its enzymatic activity leading to the phosphorylation of its downstream substrates. Detecting the phosphorylation profile of Akt with cIEF immunoassays have been performed in multiple independent studies. In the liver tissues of control C57BL/6J mice, the pI profile of Akt exhibited a triplet peak that spanned from pI 5.5 to 5.9 and an additional single peak that centered around pI 6.2 (FIG. 13A-13D). Based on previous studies, the single peak for unphosphorylated Akt and the triplet peak was assigned for the phosphorylated isoforms of Akt. Akt phosphorylation level in the liver tissues of C57BL/6J+LD and C57BL/6J+F mice were both approximately 30% lower compared to C57BL/6J mice (FIG. 13E). Akt phosphorylation level was nearly identical in the liver tissues of UPase1-TG mice compared to C57BL/6J mice. Akt phosphorylation level was approximately 50% lower in C57BL/6J+HI-D compared to C57BL/6J+LD mice.

Detecting Changes in the Phosphorylation Profile of ERK1/2 with cIEF Immunoassays.

Extracellular-signal-regulated kinases 1 and 2 (ERK1/2) participate in the signaling and regulation of cellular growth and differentiation. cIEF immunoassays have been employed to resolve single and double phosphorylated isoforms of ERK1 and ERK2. Using previously established pI values, peaks at 5.8 and 6.6 were assigned to unmodified ERK1 and ERK2, respectively (FIG. 14A-D). All other peaks were assigned to phosphorylated isoforms of ERK1/2. Quantitative analysis of areas under the curve revealed approximately 90% and 30% increases for ERK1/2 phosphorylated isoforms in CS7BL/6J+LD and CS7BL/6J+F mice compared to control CS7BL/6J mice, respectively (FIG. 14E). The level of phosphorylated ERK1/2 isoforms in CS7BL/6J+HFD mice was nearly 80% lower compared to CS7BL/6J+LD.

What is claimed is:

1. A method of determining a sub-classification of non-alcoholic fatty liver disease (NAFLD) comprising:
    measuring the activity of a metabolic and/or signaling pathway protein in liver tissue obtained from a subject, wherein the activity is measured using a capillary isoelectric focusing (cIEF) immunoassay, wherein the activity is defined by a post-translational modification chosen from methylation, glycosylation, and phosphorylation;
    detecting changes in isoelectric point (pI) of the metabolic and/or signaling pathway protein;
    quantifying the post-translational modification of the metabolic and/or signaling pathway protein by comparing the pI of the metabolic and/or signaling pathway protein with a normal pI for the metabolic and/or signaling pathway protein;
    creating a post-translational modification profile for the metabolic and/or signaling pathway protein; and
    identifying an abnormal post-translationally modified protein, wherein a change in pI of 10% or more from the normal pI indicates the presence of an abnormal post-translational modification.

2. The method of claim 1, wherein the change in pI 10% or more from the normal pI is determined by the ratio of the area under the curve (AUC) of total post-translational modified protein to the AUC of total protein (modified and unmodified).

3. The method of claim 1, wherein the sub-classification is identified as abnormal insulin signaling as characterized by the abnormal post-translational modification (% PTM) of Akt.

4. The method of claim 1, wherein the sub-classification is identified as abnormal glycolysis and lipogenesis as characterized by the abnormal % PTM of ChREBP.

5. The method of claim 1, wherein the sub-classification is identified as abnormal peroxisomal very long chain fatty acid (3-oxidation as characterized by the abnormal % PTM of EHHADH.

6. The method of claim 1, wherein the sub-classification is identified as abnormal cell growth and differentiation as characterized by the abnormal % PTM of ERK1 and ERK2.

7. The method of claim 1, wherein the sub-classification is identified as abnormal long-chain fatty acid transport as characterized by the abnormal % PTM of FABP1 and/or FABP5.

8. The method of claim 7, wherein the % PTM of FABP1 is abnormal and of FABP5 is normal.

9. The method of claim 7, wherein the % PTM of FABP5 is abnormal and of FABP1 is normal.

10. The method of claim 1, wherein the sub-classification is identified as abnormal gluconeogenesis as characterized by the abnormal % PTM of FOX01.

11. The method of claim 1, wherein the sub-classification is identified as abnormal glycogen biosynthesis as characterized by the abnormal % PTM of GSK3r3.

12. The method of claim 1, wherein the sub-classification is identified as abnormal ketogenesis as characterized by the abnormal % PTM of HMGCS2.

13. The method of claim 1, wherein the sub-classification is identified as abnormal mitochondrial long-chain fatty acid f3-oxidation as characterized by the abnormal % PTM of LCAD.

14. The method of claim 1, wherein the sub-classification is identified as abnormal cholesterol biosynthesis as characterized by the abnormal % PTM of LCAT.

15. The method of claim 1, wherein the sub-classification is identified as abnormal glycolysis as characterized by the abnormal % PTM of PFKI.

16. A method of treating non-alcoholic fatty liver disease (NAFLD) in a patient comprising:
   obtaining a capillary isoelectric focusing (cIEF) profile using a cIEF immunoassay of a sample obtained from the patient, wherein the cIEF profile includes isoelectric point (pI) information for one or more proteins, wherein the one or more proteins are components of a metabolic and/or signaling pathway related to an NAFLD pathology;
   comparing the pI of the one or more proteins with a normal pI for the one or more proteins;
   identifying a protein with an isoelectric point that deviates from the normal pI, wherein a change in pI of 10% or more from the normal pI indicates the presence of an abnormal post-translational modification; and
   selecting and administering an effective amount of a therapeutic agent selected from agents that target a metabolic and/or signaling pathway identified as being abnormal.

17. The method of claim 16, wherein the pathway is glycolysis and lipogenesis, and the pathway protein is ChREBP.

18. The method of claim 16, wherein the pathway is peroxisomal very long chain fatty acid 13-oxidation, and the pathway protein is EHHADH.

19. The method of claim 16, wherein the pathway is cell growth and differentiation, and the pathway proteins are ERK1 and ERK2.

20. The method of claim 16, wherein the pathway is long-chain fatty acid transport, and the pathway proteins are FABP1 and FABP5.

21. The method of claim 16, wherein the pathway is long-chain fatty acid transport, and the pathway protein is FABP1.

22. The method of claim 16, wherein the pathway is long-chain fatty acid transport, and the pathway protein is FABP5.

23. The method of claim 16, wherein the pathway is gluconeogenesis, and the pathway protein is FOX01.

24. The method of claim 16, wherein the pathway is glycogen biosynthesis, and the pathway protein is GSK3f3.

25. The method of claim 16, wherein the pathway is ketogenesis, and the pathway protein is HMGCS2.

26. The method of claim 16, wherein the pathway is mitochondrial long chain fatty acid 13-oxidation, and the pathway protein is LCAD.

27. The method of claim 16, wherein the pathway is cholesterol biosynthesis, and the pathway protein is LCAT.

28. The method of claim 16, wherein the pathway is glycolysis, and the pathway protein is PFK1.

29. A method for determining the prognosis of non-alcoholic fatty liver disease (NAFLD) in a patient comprising:
   measuring the activity of a metabolic and/or signaling pathway protein in liver tissue obtained from the patient, wherein the activity is measured using a capillary isoelectric focusing (cIEF) immunoassay, wherein the activity is a post-translational modification chosen from acetylation, glycosylation, and phosphorylation;
   detecting changes in isoelectric point (pI) of the metabolic and/or signaling pathway protein;
   quantifying the post-translational modification of the metabolic and/or signaling pathway protein by comparing the pI of the metabolic and/or signaling pathway protein with a normal pI for the metabolic and/or signaling pathway protein;
   creating a post-translational modification profile for the metabolic and/or signaling pathway protein; and
   comparing the post-translational modification profile of the patient with a post-translational modification profile of a patient with NAFLD and known disease progression and determining the prognosis based on the closest profile match.

30. The method of claim 29, wherein the pathway is insulin signaling, and the pathway protein is Akt.

31. The method of claim 29, wherein the pathway is glycolysis and lipogenesis, and the pathway protein is ChREBP.

32. The method of claim 29, wherein the pathway is peroxisomal very long chain fatty acid f3-oxidation, and the pathway protein is EHHADH.

33. The method of claim 29, wherein the pathway is cell growth and differentiation, and the pathway proteins are ERK1 and ERK2.

34. The method of claim 29, wherein the pathway is long-chain fatty acid transport, and the pathway proteins are FABP1 and FABP5.

35. The method of claim 29, wherein the pathway is long-chain fatty acid transport, and the pathway protein is FABP1.

36. The method of claim 29, wherein the pathway is long-chain fatty acid transport, and the pathway protein is FABP5.

37. The method of claim 29, wherein the pathway is gluconeogenesis, and the pathway protein is FOXO1.

38. The method of claim 29, wherein the pathway is glycogen biosynthesis, and the pathway protein is GSK3f3.

39. The method of claim 29, wherein the pathway is ketogenesis, and the pathway protein is HMGCS2.

40. The method of claim 29, wherein the pathway is mitochondrial long chain fatty acid 13-oxidation, and the pathway protein is LCAD.

41. The method of claim 29, wherein the pathway is cholesterol biosynthesis, and the pathway protein is LCAT.

42. The method of claim 29, wherein the pathway is glycolysis, and the pathway protein is PFKI.

\* \* \* \* \*